(12) United States Patent  
Figulla et al.

(10) Patent No.: US 12,257,147 B2
(45) Date of Patent: Mar. 25, 2025

(54) SYSTEM FOR TREATING, PREVENTING AND/OR REPLACING A HEART VALVE, IN PARTICULAR AN INFLAMED, INFECTED, THROMBOSED OR DEGENERATED HEART VALVE

(71) Applicant: DEVIE MEDICAL GMBH, Jena (DE)

(72) Inventors: Hans-Reiner Figulla, Jena (DE); Raphael Andreas Seidel, Weimar (DE); Sharath Chandra Chavalla, Jena (DE)

(73) Assignee: DEVIE MEDICAL GMBH, Jena (DE)

( * ) Notice: Subject to any disclaimer, the term of this patent is extended or adjusted under 35 U.S.C. 154(b) by 0 days.

(21) Appl. No.: 18/276,818

(22) PCT Filed: Feb. 10, 2022

(86) PCT No.: PCT/EP2022/053299
§ 371 (c)(1),
(2) Date: Aug. 10, 2023

(87) PCT Pub. No.: WO2022/171764
PCT Pub. Date: Aug. 18, 2022

(65) Prior Publication Data
US 2024/0238083 A1 Jul. 18, 2024

(30) Foreign Application Priority Data
Feb. 10, 2021 (DE) .............................. 102021000811

(51) Int. Cl.
*A61F 2/24* (2006.01)
(52) U.S. Cl.
CPC .... *A61F 2/2418* (2013.01); *A61F 2210/0004* (2013.01); *A61F 2210/0014* (2013.01);
(Continued)

(58) Field of Classification Search
CPC ............ A61F 2/2418; A61F 2210/0004; A61F 2210/0014; A61F 2220/0008; A61F 2250/0048; A61F 2250/0067
See application file for complete search history.

(56) References Cited

U.S. PATENT DOCUMENTS

| 6,730,118 B2 | 5/2004 | Spenser et al. |
| 2001/0044656 A1 | 11/2001 | Williamson et al. |

(Continued)

FOREIGN PATENT DOCUMENTS

| CA | 3210896 A1 | 8/2022 |
| CN | 101180010 A | 5/2008 |

(Continued)

OTHER PUBLICATIONS

National Intellectual Property Administration, R.P.C., "Notice of Grant regarding China Patent Application No. 201980066868.2," Apr. 15, 2024, 11 pages, published in China (with translation).

(Continued)

*Primary Examiner* — Suzette J Gherbi
(74) *Attorney, Agent, or Firm* — NOD Law PC

(57) ABSTRACT

An anchoring for heart valve prostheses includes a stent framework, for attaching heart valve leaflets to an inner side, and compartmentalization clips, connected with the stent framework at a first end region and having a free second end region. The anchoring exhibits a primary form and reversibly transformable into a delivery form for the minimally invasive introduction into the body of the patient by elastic deformation and/or compression of certain regions or elements. The compartmentalization clips are arcuately shaped between the first and second end regions in the primary form and are elastically foldable such that the compartmentalization clips extend in a flat manner between the first and second end regions in the delivery form. The anchoring has a separation structure connected with the stent framework (Continued)

and the compartmentalization clips to separate the areas of the native leaflets to be treated from the bloodstream when the anchoring implanted.

20 Claims, 8 Drawing Sheets

(52) U.S. Cl.
CPC .............. *A61F 2220/0008* (2013.01); *A61F 2250/0048* (2013.01); *A61F 2250/0067* (2013.01)

(56) References Cited

U.S. PATENT DOCUMENTS

| | | | |
|---|---|---|---|
| 2007/0142906 | A1 | 6/2007 | Figulla et al. |
| 2009/0319037 | A1 | 12/2009 | Rowe et al. |
| 2011/0118634 | A1 | 5/2011 | Golan et al. |
| 2011/0208298 | A1* | 8/2011 | Tuval ................ A61F 2/2418 623/2.17 |
| 2013/0035759 | A1 | 2/2013 | Gross et al. |
| 2013/0066341 | A1 | 3/2013 | Ketai et al. |
| 2014/0371845 | A1* | 12/2014 | Tuval ................ A61F 2/2436 623/2.11 |
| 2016/0228248 | A1 | 8/2016 | Rowe et al. |
| 2017/0095328 | A1 | 4/2017 | Cooper et al. |
| 2017/0128199 | A1 | 5/2017 | Gurovich et al. |
| 2017/0165058 | A1 | 6/2017 | Rothstein et al. |
| 2017/0209264 | A1* | 7/2017 | Chau ........................ A61F 2/24 |
| 2018/0000579 | A1 | 1/2018 | Lauten et al. |
| 2018/0000586 | A1* | 1/2018 | Ganesan .............. A61F 2/2409 |
| 2018/0125648 | A1 | 5/2018 | Nasr et al. |
| 2018/0206982 | A1 | 7/2018 | Haivatov et al. |
| 2018/0250126 | A1 | 9/2018 | O'Connor et al. |
| 2020/0397568 | A1* | 12/2020 | Chau ................... A61F 2/246 |
| 2021/0386541 | A1* | 12/2021 | Figulla ................ A61F 2/0077 |

FOREIGN PATENT DOCUMENTS

| | | |
|---|---|---|
| CN | 105934220 A | 9/2016 |
| CN | 106264793 A | 1/2017 |
| CN | 106572906 A | 4/2017 |
| CN | 112822991 A | 5/2021 |
| EP | 4277576 A1 | 11/2023 |
| WO | 2020074130 A1 | 4/2020 |
| WO | 2020123267 A1 | 6/2020 |
| WO | 2020234199 A1 | 11/2020 |
| WO | 2022171764 A1 | 8/2022 |

OTHER PUBLICATIONS

European Patent Office, "Communication about intention to grant a European patent," EPO notice, German only, May 6, 2022.
European Patent Office, "Communication from EPO," German only, Oct. 6, 2022.
European Patent Office, "Decision to grant," German only, Published in EU, Mar. 7, 2024.
European Patent Office, "Intention to grant," German only, Nov. 13, 2023.
Non-Final Office Action for U.S. Appl. No. 17/283,947, dated Oct. 13, 2023, 16 pages.
Office Action for Chinese Patent Application No. 201980066868.2, dated Oct. 23, 2023, with English Translation, 31 pages.
Trinks, Ole, "Filing of translated allowed claims," German only, Published in EU, Feb. 22, 2024.
WIPO, International Search Report for PCT International Application No. PCT/EP2019/058666, with translation, 8 pages, mailed Jul. 16, 2019.
European Patent Office, "(Electronic) Receipt," European Patent Register, as published Jan. 25, 2024 for EP Patent Publication No. EP4277576 (EP Patent Application No. EP22706034A, filed Feb. 10, 2022), published in EU.
European Patent Office, "Annex to the communication about intention to grant a European patent," European Patent Register, as published Mar. 19, 2024 for EP Patent Publication No. EP4277576 (EP Patent Application No. EP22706034A, filed Feb. 10, 2022), published in EU.
European Patent Office, "Annex to the communication," European Patent Register, as published Dec. 14, 2023 for EP Patent Publication No. EP4277576 (EP Patent Application No. EP22706034A, filed Feb. 10, 2022), published in EU.
European Patent Office, "Bibliographic data of the European patent application," European Patent Register, as published Mar. 19, 2024 for EP Patent Publication No. EP4277576 (EP Patent Application No. EP22706034A, filed Feb. 10, 2022), published in EU.
European Patent Office, "Communication about intention to grant a European patent," European Patent Register, as published Mar. 19, 2024 for EP Patent Publication No. EP4277576 (EP Patent Application No. EP22706034A, filed Feb. 10, 2022), published in EU.
European Patent Office, "Communication from the Examining Division," European Patent Register, as published Dec. 14, 2023 for EP Patent Publication No. EP4277576 (EP Patent Application No. EP22706034A, filed Feb. 10, 2022), published in EU.
European Patent Office, "Intention to grant (signatures)," European Patent Register, as published Mar. 19, 2024 for EP Patent Publication No. EP4277576 (EP Patent Application No. EP22706034A, filed Feb. 10, 2022), published in EU.
European Patent Office, "Text Intended for Grant (clean copy)," European Patent Register, as published Mar. 19, 2024 for EP Patent Publication No. EP4277576 (EP Patent Application No. EP22706034A, filed Feb. 10, 2022), published in EU.
European Patent Office, "Text Intended for Grant (version for approval)," European Patent Register, as published Mar. 19, 2024 for EP Patent Publication No. EP4277576 (EP Patent Application No. EP22706034A, filed Feb. 10, 2022), published in EU.
Ole Trinks, "Amended claims with annotations," European Patent Register, as published Jan. 25, 2024 for EP Patent Publication No. EP4277576 (EP Patent Application No. EP22706034A, filed Feb. 10, 2022), published in EU.
Ole Trinks, "Claims," European Patent Register, as published Jan. 25, 2024 for EP Patent Publication No. EP4277576 (EP Patent Application No. EP22706034A, filed Feb. 10, 2022), published in EU.
Ole Trinks, "Description," European Patent Register, as published Jan. 25, 2024 for EP Patent Publication No. EP4277576 (EP Patent Application No. EP22706034A, filed Feb. 10, 2022), published in EU.
Ole Trinks, "Letter accompanying subsequently filed items," European Patent Register, as published Jan. 25, 2024 for EP Patent Publication No. EP4277576 (EP Patent Application No. EP22706034A, filed Feb. 10, 2022), published in EU.
Ole Trinks, "Reply to communication from the Examining Division" European Patent Register, as published Jan. 25, 2024 for EP Patent Publication No. EP4277576 (EP Patent Application No. EP22706034A, filed Feb. 10, 2022), published in EU.
Ole Trinks, "Patentanmeldung—Änderungen" mailed Sep. 9, 2022; Published in EP (no translation available).
WIPO, "Internationaler Recherchenbericht," "Schriftlicher Bescheid der Internationalen Recherchenbenorde," mailed Jul. 12, 2022, published Aug. 18, 2022 in EP.
WIPO, "Internationaler Vorlaufiger Bericht uber die Patentierbarkeit," mailed Dec. 22, 2022, Published in EP.

\* cited by examiner

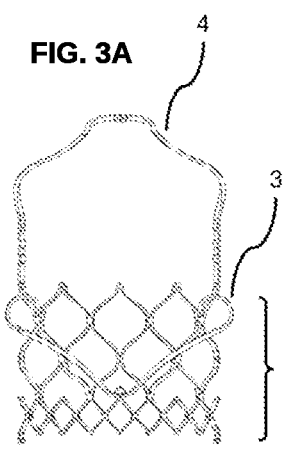
FIG. 3A
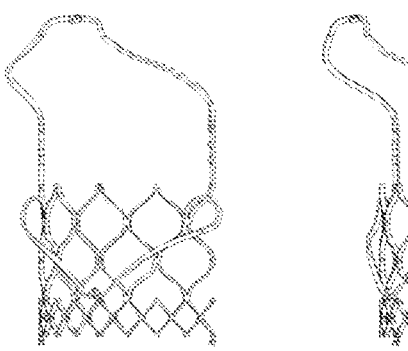
FIG. 3B
(30° rotated view)
FIG. 3C
(60° rotated view)
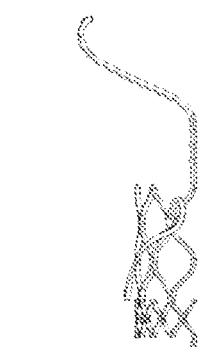
FIG. 3D
(90° rotated view)
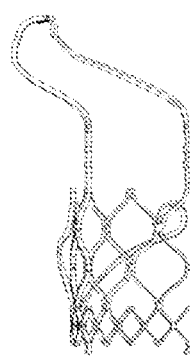
FIG. 3E
(120° rotated view)
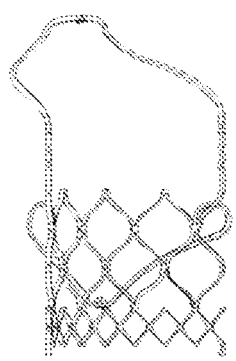
FIG. 3F
(150° rotated view)
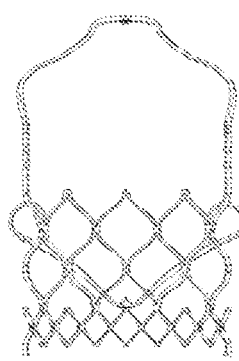
FIG. 3G
(180° rotated view)
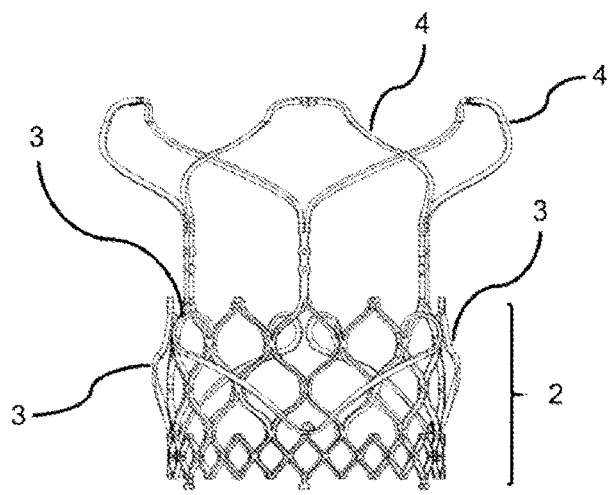
FIG. 4

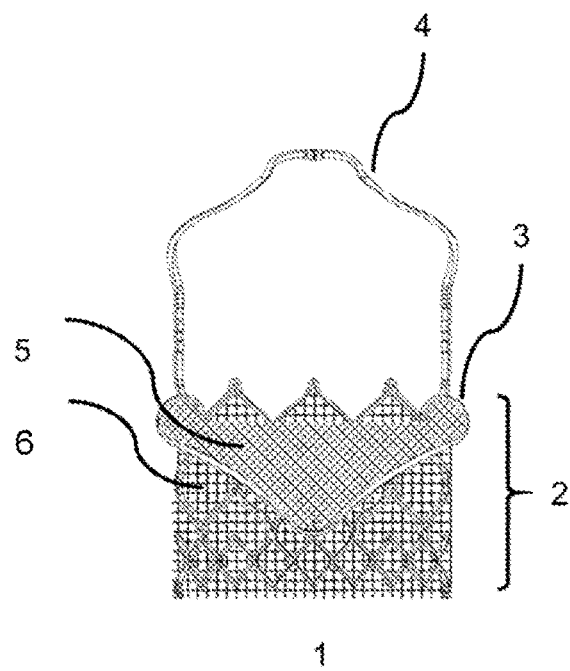
FIG. 7
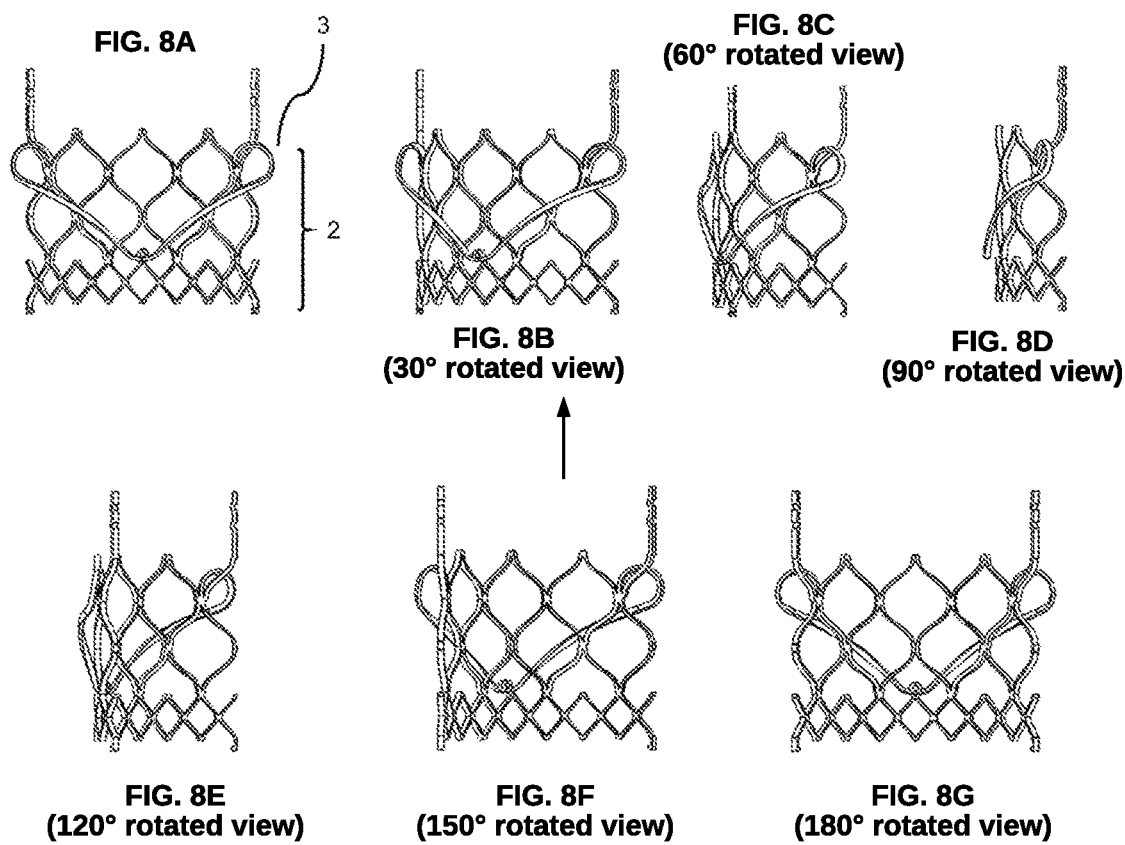
FIG. 8A
FIG. 8B
(30° rotated view)
FIG. 8C
(60° rotated view)
FIG. 8D
(90° rotated view)
FIG. 8E
(120° rotated view)
FIG. 8F
(150° rotated view)
FIG. 8G
(180° rotated view)

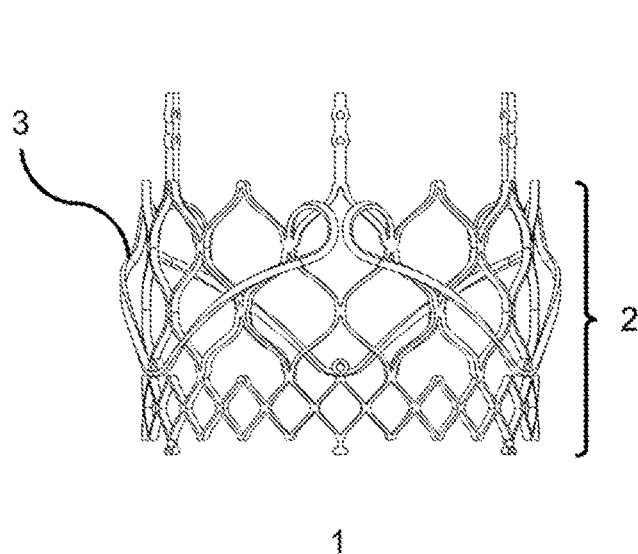 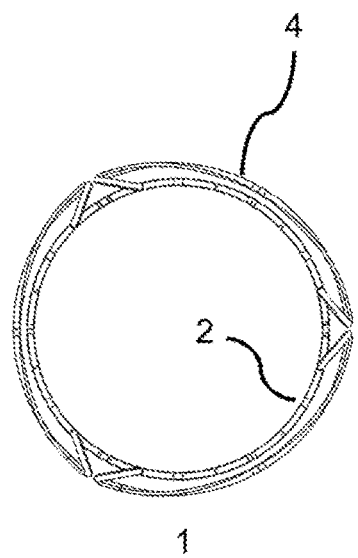
FIG. 9A    FIG. 9B
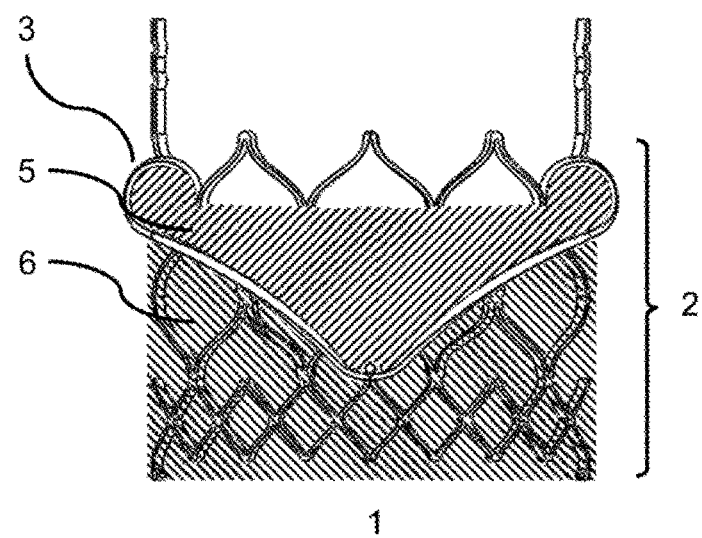
FIG. 10

FIG. 11A
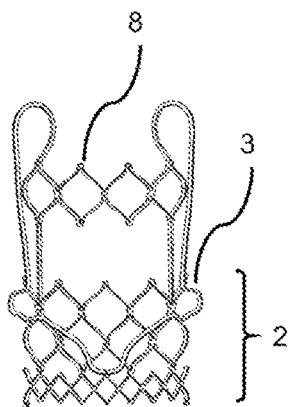
FIG. 11B
(30° rotated view)
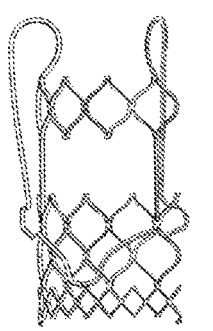
FIG. 11C
(60° rotated view)
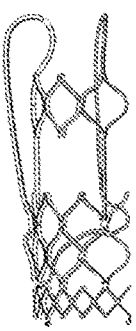
FIG. 11D
(90° rotated view)
FIG. 11E
(120° rotated view)
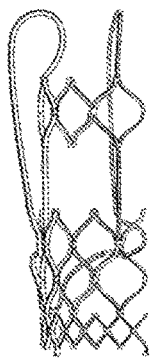
FIG. 11F
(150° rotated view)
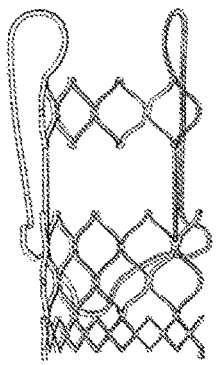
FIG. 11G
(180° rotated view)
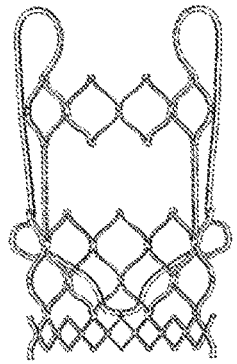
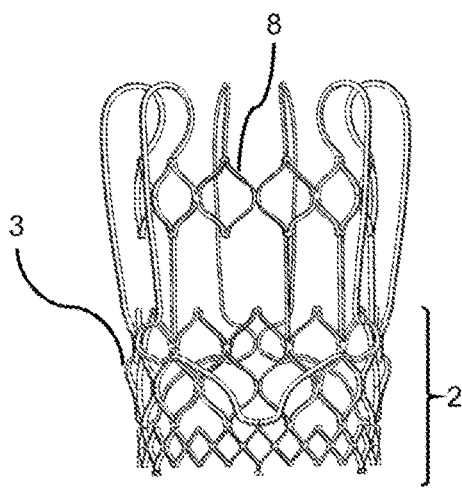
FIG. 12A
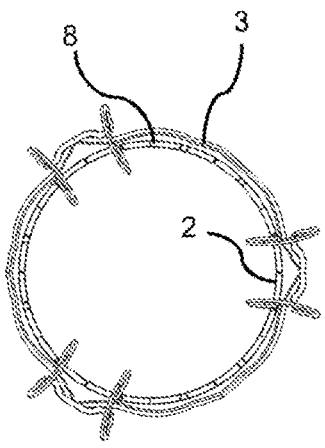
FIG. 12B

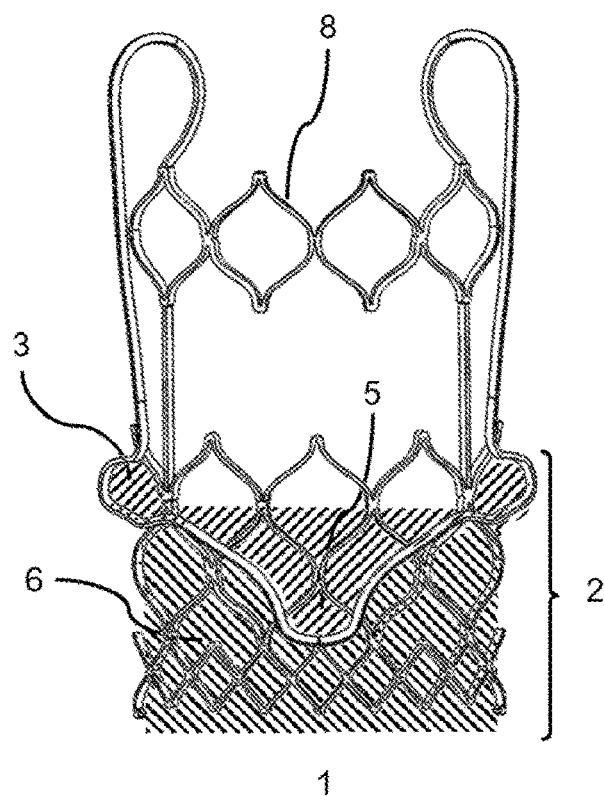
FIG. 13
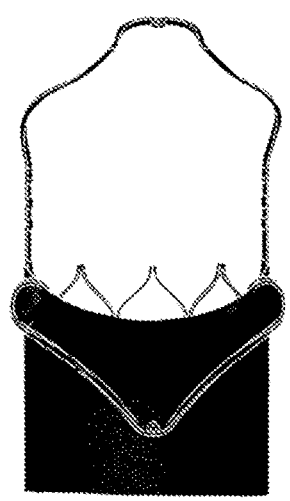   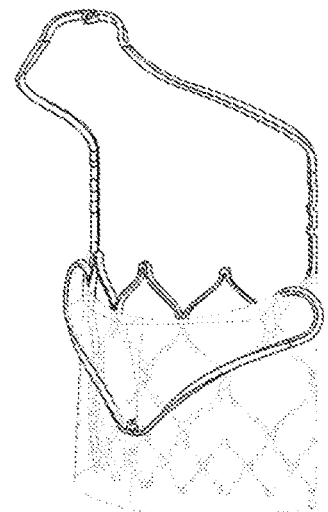   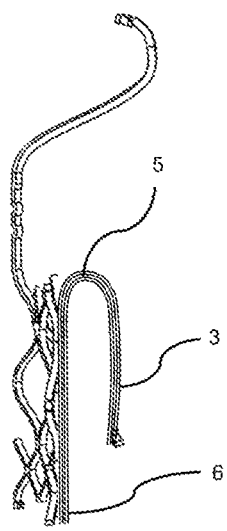
FIG. 14A　　　FIG. 14B　　　FIG. 14C

SYSTEM FOR TREATING, PREVENTING AND/OR REPLACING A HEART VALVE, IN PARTICULAR AN INFLAMED, INFECTED, THROMBOSED OR DEGENERATED HEART VALVE

REFERENCE TO RELATED APPLICATIONS

The present application is a 35 U.S.C. 371 national stage application of PCT International Application No. PCT/EP2022/053299, filed on 10 Feb. 2022, which claims priority from German Patent Application No. 102021000811, filed on 10 Feb. 2021. The above referenced applications are incorporated herein in their entirety by reference.

DESCRIPTION OF RELATED ART

There are currently numerous stent systems for supporting and keeping vessels open as well as for introducing or replacing vascular valves such as heart valves, for example. These systems can on the one hand be introduced surgically, for example by way of open-heart surgery or in a minimally invasive procedure and, on the other hand, they can also be introduced directly into the cardiovascular system via catheter-based arterial or venous access. The catheter-guided implants frequently exhibit a balloon-expandable metal frame or a self-expandable metal frame consisting of a shape memory alloy for the stents/heart valves. Furthermore, partially thin layers or tissue-like structures are affixed or deposited that, on the one hand, are intended to facilitate the ingrowth of the implant and, on the other hand, keep the lumen of the implant open and, particularly in the case of heart valves, are intended to prevent blood flow around the valve (i.e., paravalvular leak). The catheter-introduced heart valve implants are characterized by reducing the stress on a patient compared to the surgical procedure opening the thorax. In the case of native or prosthetic heart valve infections accompanied by valve destruction, so-called native or prosthetic endocarditis (NVE, PVE), catheter-guided heart valve replacement is absolutely contraindicated since doing so cuts off infected areas from the blood circulation and it can be assumed that the infection will spread such that the patient's situation will worsen. Moreover, when conventional catheter-guided heart valves are inserted, infectious bacterial deposits on the native heart valve leaflets (so-called vegetation) can tear away and embolize into the bloodstream.

In contrast to catheter-based heart valve replacement, the open surgical procedure using a heart-lung machine, which needs to be performed in a majority of endocarditis patients despite multimorbidity, can remove the infected material. However, these infective endocarditis surgeries are associated with high surgical risks due to the patient comorbidity associated with endocarditis such that the average hospital mortality with NVE and PVE is roughly 20%. Published patent application WO 2020/074130 A1 further reflects the current prior art. The frame structures introduced in WO 2020/074130 A1 for prosthetic heart valves to be used in the replacement of inflamed, thrombosed or degenerated heart valves are of a two-part construction, whereby the infected areas are compartmentalized and treated between the one member bearing the new heart valve leaflet and the other member acting as an abutment. This two-part solution has the following disadvantages. The introduction of two parts is more time-consuming and technically complicated since a positive and/or non-positive connection needs to be established between the two parts during catheter-guided implantation for efficient compartmentalization. Even small gaps between the two parts could foster at least partial flushing of the active agents in the compartmentalized pre-lumen and thus jeopardize treatment needing sufficiently high enough concentrations. Furthermore, two-part solutions may show signs of abrasion on both parts at the connecting or contact points due to the constant pulsatile motion of the beating heart, which could lead to material fatigue or embolization.

SUMMARY OF THE INVENTION

An anchoring for heart valve prostheses for the treatment, prevention and/or replacement of a heart valve, in particular an inflamed, infected, thrombosed and/or degenerated heart valve, wherein the anchoring exhibits a primary form and is able to be reversibly transformed into a delivery form for the minimally invasive introduction of the anchoring into the body of the patient and that by elastic deformation and/or compression of at least regions or elements of the anchoring, wherein the anchoring includes the following:
 a stent framework (2) designed to attach at least two heart valve leaflets to an inner side, wherein the stent framework has a proximal end and a distal end; and
 at least two compartmentalization clips (3), each connected to the stent framework at a first end region and having a free second end region,
 wherein the compartmentalization clips (3) are arcuately shaped between the first and second end regions in the primary form of the anchoring.

In an embodiment, the compartmentalization clips (3) at least partially overlap the stent framework, particularly in the radial and proximal (close to the heart) direction of the stent framework, in the primary form of the anchoring.

In other embodiments, the compartmentalization clips (3) are able to be elastically folded over such that the compartmentalization clips extend in at least substantially flat manner between the first and second end regions in the delivery form of the anchoring.

In embodiments, the compartmentalization clips include arms includes an at least partial twisting in the primary form of the anchoring.

In embodiments, the compartmentalization clips (2) exhibit a first clip surface and a second clip surface oppositely disposed from the first clip surface, and wherein the first clip surface at the free second end area of the compartmentalization clips is directed at least substantially radially inward, in particular toward a longitudinal axis of the anchoring, in both the primary form as well as the delivery form of the anchoring.

In embodiments, the compartmentalization clips (2) exhibit a first clip surface and a second clip surface oppositely disposed from the first clip surface, and wherein the first clip surface is directed outward and the second clip surface directed inward in the primary form and the first surface is directed inward and the second surface directed outward in the delivery form.

In embodiments, the anchoring is designed to hold, in particular clamp, native leaflets and/or infectious and/or thrombotic deposits/vegetation of the diseased heart valve between the stent framework and the compartmentalization clips (3) when the anchoring is in an implanted state.

In embodiments, the anchoring includes a separation structure which is connected to the stent framework (2) and the compartmentalization clips (3) such that the separation structure (5) separates the areas of the native leaflets to be treated from the bloodstream when the anchoring is in the implanted state (FIG. 13).

In embodiments, the separation structure exhibits a first structural surface directed radially inward in the delivery form of the anchoring, in particular toward a longitudinal axis of the anchoring, and a second structural surface opposite from the first structural surface, and wherein at least the second structural surface includes a matrix which contains and can release antibiotic, antithrombotic and/or thrombolytic agents ((6) in FIG. 13, 14).

In embodiments, the stent framework and the compartmentalization clips are of a single-piece construction.

In embodiments, the stent framework and/or the compartmentalization clips is/are made from a compressible material.

In embodiments, the stent framework and/or the compartmentalization clips is/are made from a self-expanding material.

In embodiments, the stent framework and the compartmentalization clips are made from at least two connected or connectable pieces of a self-expandable material.

In embodiments, the stent framework and the compartmentalization clips are made from at least two connected or connectable pieces, and the stent framework is made from a balloon-expandable material and the compartmentalization clips from a self-expandable material.

In embodiments, the stent framework and/or the compartmentalization clips consist of a shape memory alloy, in particular nitinol.

In embodiments, the at least two compartmentalization clips (3) overlap the stent framework (2) in the primary form of the anchoring such that no part of the compartmentalization clips protrudes beyond the distal end of the stent framework (2).

In certain embodiments, a catheter for introducing an anchoring for heart valve prostheses into the body of a patient is described. The catheter aids in the anchoring being able to be introduced minimally invasively into the body of the patient in a delivery form and transformed into an implanted state in the implantation site on the diseased heart valve, and wherein the anchoring may include the following:
  a stent framework (2) designed to attach at least two heart valve leaflets to an inner side, wherein the stent framework has a proximal end and a distal end;
  at least two compartmentalization clips (3) connected to the stent framework and which at least partially overlap the stent framework (2) in the primary form of the anchoring in order to hold, in particular clamp, native leaflets and/or infectious and/or thrombotic deposits/vegetation of the diseased heart valve between the stent framework and the compartmentalization clips (3),
  wherein the catheter has a catheter tip able to be manipulated via a handle of the catheter (20) such that the implant (1) is incrementally releasable from the catheter tip.

In embodiments, the catheter tip is of a divided design such that the at least two compartmentalization clips (2) can be incrementally released from the catheter tip one after the other and the stent framework then released subsequently.

In embodiments, the partitioned catheter tip has a tapered sleeve which is designed to cover the anchoring during introduction and which is retractable by means of the handle in order to incrementally release the compartmentalization clips.

In embodiments, the catheter is designed to rotate the anchoring by the handle in order to align the compartmentalization clips with the pockets/leaflets of the native valve.

In certain embodiments, a system for the treatment, prevention and/or replacement of a heart valve, in particular an inflamed, infected, thrombosed or degenerated heart valve is disclosed. The system may include an anchoring and a catheter as described above, wherein the anchoring is designed to be receivable in the catheter tip, particularly in the delivery form of the anchoring, and wherein the catheter tip is designed to accommodate the anchoring (1), particularly in the delivery form of the anchoring.

In certain embodiments, a method for the treatment, prevention and/or replacement of a heart valve, in particular an inflamed, infected, thrombosed or degenerated heart valve is disclosed. The method may include the following:
  introducing an anchoring via a catheter as described above;
  releasing the compartmentalization clips (3);
  aligning the compartmentalization clips on a first side of the native leaflets of the diseased heart valve; and
  releasing the stent framework (2) on a second side of the native leaflets opposite from the first side and thereby clamping the leaflets of the diseased heart valve (e.g., FIG. 14).

In embodiments, the method may include releasing antibiotic, antithrombotic, thrombolytic and/or cell growth-inhibiting agents, whereby the release ensues in situ.

In embodiments, the compartmentalization clips (3) are incrementally released one after the other (e.g., FIG. 15A-E).

In certain embodiments, an anchoring for heart valve prostheses, in particular for heart valve prostheses for the treatment, prevention and/or replacement of a heart valve, in particular an inflamed, infected, thrombosed or degenerated heart valve is disclosed. The anchoring exhibits a primary form and may be reversibly transformed, and in particular by elastic deformation and/or compression of at least regions or elements of the anchoring, into a delivery form for the minimally invasive introduction of the anchoring into the body of the patient. The anchoring may include the following:
  a stent framework (2) designed to attach at least two heart valve leaflets to an inner side, wherein the stent framework has a proximal end and a distal end; and
  at least two stabilization arches (4) which protrude beyond the distal end of the stent framework (2) and are designed to be supported on a vascular wall in the implanted state of the anchoring such that the anchoring is centrally aligned in the blood vessel to be implanted subsequent the release of the stabilization arches (4).

In embodiments, the length and/or shape of the at least two stabilization arches is/are designed so as to be distinguishable in an X-ray and be able to be released one after the other during implantation.

In embodiments, the stabilization arches have a proximal end connected to the distal end of the stent framework (2) and a distal end which protrudes beyond the distal end of the stent framework, and wherein the stabilization arches are connected together at the distal end by struts, diamond-like or other elements which are designed to increase the radial stability and enable a centralizing of the anchoring in the blood vessel to be implanted (8) (e.g., FIGS. 11-13).

In embodiments, the anchoring includes a separation structure connected to the stent framework (2) such that the separation structure separates the areas of the native leaflets to be treated from the bloodstream in the expanded state of the anchoring.

In embodiments, the separation structure includes an at least external matrix (6) which contains and can release antibiotic, antithrombotic and/or thrombolytic agents.

In embodiments, the stent framework and the stabilization arches are of a single-piece construction.

In embodiments, the stent framework and/or the stabilization arches is/are made from a compressible material.

In embodiments, the stent framework and/or the stabilization arches is/are made from a self-expanding material.

In embodiments, the stent framework and/or the stabilization arches includes a shape memory alloy, such as nitinol.

In embodiments, the anchoring has at least two compartmentalization clips (3), each connected to the stent framework (2) at a first end region and having a free second end region, wherein the compartmentalization clips (3) are arcuately shaped between the first and second end regions in the primary form of the anchoring.

In embodiments, the compartmentalization clips (3) at least partially overlap the stent framework in the primary form of the anchoring.

In embodiments, the compartmentalization clips (3) are able to be folded over such that the compartmentalization clips extend in at least substantially flat manner between the first and second end regions in the delivery form of the anchoring.

In certain embodiments an anchoring for heart valve prostheses, in particular for heart valve prostheses for the treatment, prevention and/or replacement of a heart valve, particularly an inflamed, infected, thrombosed or degenerated heart valve is described. The anchoring exhibits a primary form and may be reversibly transformed, and in particular by elastic deformation and/or compression of at least regions or elements of the anchoring, into a delivery form for the minimally invasive introduction of the anchoring into the body of the patient. The anchoring may include the following:

a stent framework (2) designed to attach at least two heart valve leaflets to an inner side, wherein the stent framework has a proximal end and a distal end;

at least two compartmentalization clips (3) connected to the stent framework and which at least partially overlap the stent framework (2) in the primary form of the anchoring in order to hold, in particular clamp, native leaflets and/or infectious and/or thrombotic deposits/vegetation of the diseased heart valve between the stent framework (2) and the compartmentalization clips (3); and a separation structure connected to the stent framework (2) and the compartmentalization clips (3) such that when in the implanted state, the separation structure separates the areas of the native leaflets to be treated from the bloodstream.

In embodiments, the separation structure exhibits a first structural surface directed radially inward in the delivery form, in particular toward a longitudinal axis of the anchoring, and a second structural surface opposite from the first structural surface, and wherein at least the second structural surface includes a matrix which contains and can release antibiotic, antithrombotic and/or thrombolytic agents.

In embodiments, the at least one active substance-containing matrix is bioresorbable.

In embodiments, the stent framework and the compartmentalization clips are of a single-piece construction.

In embodiments, the stent framework and/or the compartmentalization clips is/are made from a compressible material.

In embodiments, the stent framework and/or the compartmentalization clips is/are made from a self-expandable material.

In embodiments, the stent framework and the compartmentalization clips are made from at least two connected or connectible pieces of a self-expandable material.

In embodiments, the stent framework and the compartmentalization clips are made from at least two connectable pieces connected together and the stent framework is made from a balloon-expandable material and the compartmentalization clips from a self-expandable material.

In embodiments, the stent framework and/or the compartmentalization clips consist of a shape memory alloy, in particular nitinol.

In embodiments, the at least two compartmentalization clips (3) have a first end region which is connected to the stent framework (2) and a free second end region, wherein the compartmentalization clips (3) are arcuately shaped between the first and second end regions in the primary form of the anchoring.

In embodiments, the compartmentalization clips (3) at least partially overlap the stent framework (2) in the primary form of the anchoring.

In embodiments, the compartmentalization clips (3) are foldable such that the compartmentalization clips extend in at least substantially flat manner between the first and second end regions in the delivery form of the anchoring.

In embodiments, the anchoring has three compartmentalization clips (3).

In embodiments, the at least two compartmentalization clips (3) are radially spaced apart from each other and connected together via the stent framework (2) in the expanded state of the anchoring.

In embodiments, the stent framework exhibits a first cell structure made of struts at its proximal end and a second cell structure made of struts at its distal end, wherein the first and the second cell structure are of different designs.

In embodiments, the first cell structure has a higher density of struts than the second cell structure.

In embodiments, the anchoring is cut from a shape memory alloy tube.

In certain embodiments, a heart valve prosthesis, in particular for heart valve prostheses for the treatment, prevention and/or replacement of a heart valve, particularly an inflamed, infected, thrombosed or degenerated heart valve is disclosed. The heart valve prosthesis may include an anchoring as described above and a stent framework of the anchoring including an inner side to which at least two heart valve leaflets may be affixed thereto.

BRIEF DESCRIPTION OF DRAWINGS

FIGS. 3A-3G show a one-third portion of the frame structure of the heart valve prosthesis of the exemplary embodiment of FIG. 1 after the shaping process, wherein the individual elements of the FIG. 3A to 3G) each represents the same element and each partial illustration view is axially rotated by a further 30°.

FIG. 4 shows a side view of the frame structure of the heart valve prosthesis of an exemplary embodiment from FIG. 1.

FIG. 7 shows a third of an embodiment in which both the lower portion of the stent framework as well as the compartmentalization clips are affixed over the area by a thin layer as a barrier to the bloodstream and/or the areas containing active substance.

FIGS. 8A-8G show rotated view of a one-third portion of a frame structure of a heart valve prosthesis, in accordance with a further embodiment, wherein the frame of the heart valve prosthesis is formed without stabilization arches.

FIGS. 9A and 9B show the entire frame structure of the exemplary embodiment from FIGS. 8A-8G, wherein FIG. 9A shows a view from the front (frontal) and FIG. 9B shows a view from above (apical).

FIG. 10 shows a part of the exemplary embodiment from FIGS. 8A-8G and 9A-9B, shown here including a separating layer and active substance-releasing matrices, both of which extend continuously over the arches of the compartmentalization clips from the stent framework.

FIGS. 11A-11G show a one-third portion of a frame structure of a heart valve prosthesis, in accordance with a further embodiment, shown in the expanded and folded-over state. The compartmentalization clips are configured to first extend upward from the stent framework in a long arc and then reach back down again. Further, starting from the stent framework, the separating layer and the active substance-releasing layer matrices are only affixed in the lower area of the compartmentalization clips. Structures further connect the arches together in the upper region in this exemplary embodiment for stabilization and application of radial force.

FIGS. 12A-12B show the entire frame of the exemplary embodiment from FIGS. 11A-11G, wherein FIG. 12A shows a view from the front (frontal) and FIG. 12B shows a view from above (apical).

FIG. 13 shows a part of the exemplary embodiment from FIGS. 11A-11G and 12A-12B, shown here including a separating layer and active substance-releasing matrices, both of which extend continuously over the arches of the compartmentalization clips from the stent framework.

FIGS. 14A-14C show a front, a partially transparent, and a side view, respectively, of a portion of the stent framework, shown here with the arches of the compartmentalization clips, a separating layer affixed thereto, and a matrix containing an active substance.

LIST OF REFERENCE NUMERALS

Figure 1:
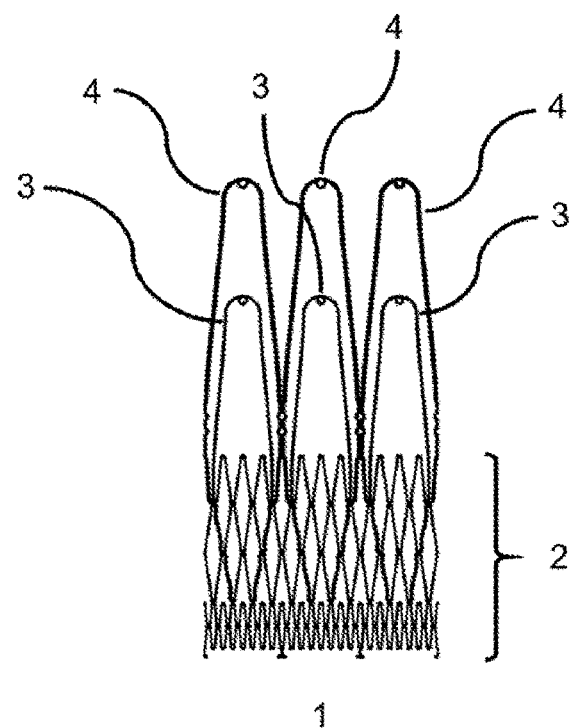
FIG. 1 shows the sectioned metal frame of a heart valve prosthesis, in accordance with an embodiment, with three-fold rotational symmetry to the heart valve prosthesis for use in a three-leaflet heart valve. Illustrated here is the cutting pattern for a tubular material brought into two-dimensional depiction.
Figure 2:
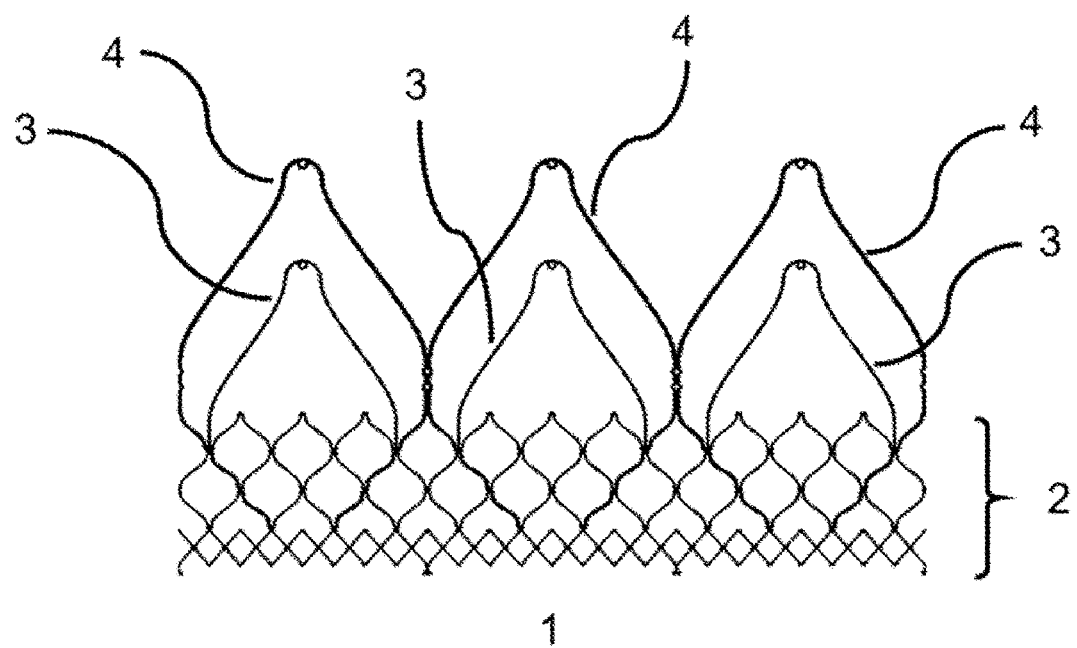
FIG. 2 shows a two-dimensional depiction of the frame structure of the heart valve prosthesis of the exemplary embodiment of FIG. 1 after having been radially expanded in the course of the shaping process and the compartmentalization clips having been folded downward.
Figure 5:
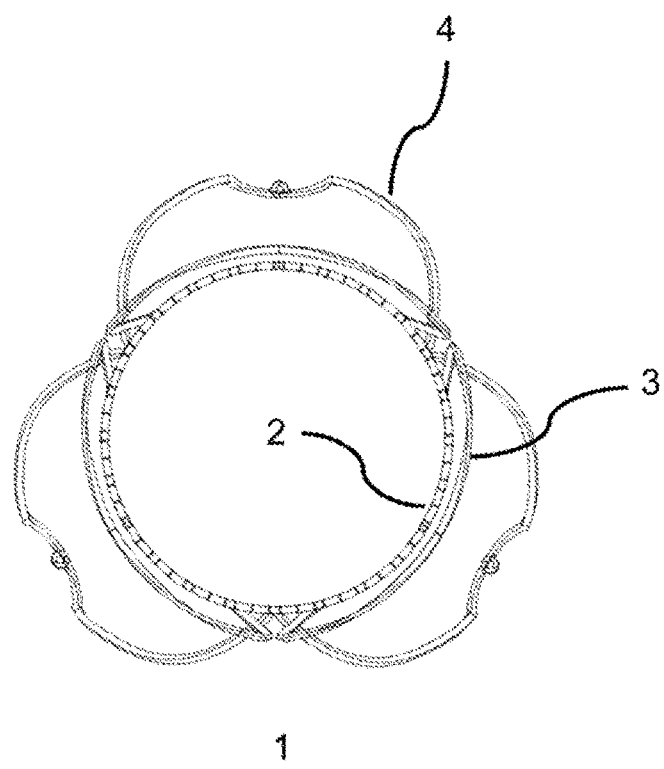
FIG. 5 shows a top view onto the frame structure of the heart valve prosthesis of an exemplary embodiment.
Figure 6:
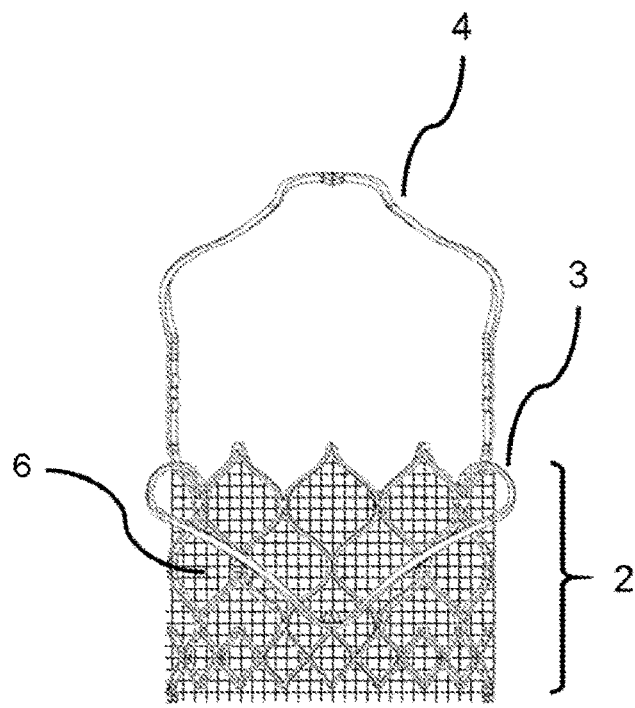
FIG. 6 shows a side view of a one-third portion of the frame structure of the heart valve prosthesis of an embodiment, in which the lower portion of the stent framework, albeit not the compartmentalization clips, is affixed by a thin layer as a barrier to the bloodstream and/or the areas containing active substance.
Figure 15E:
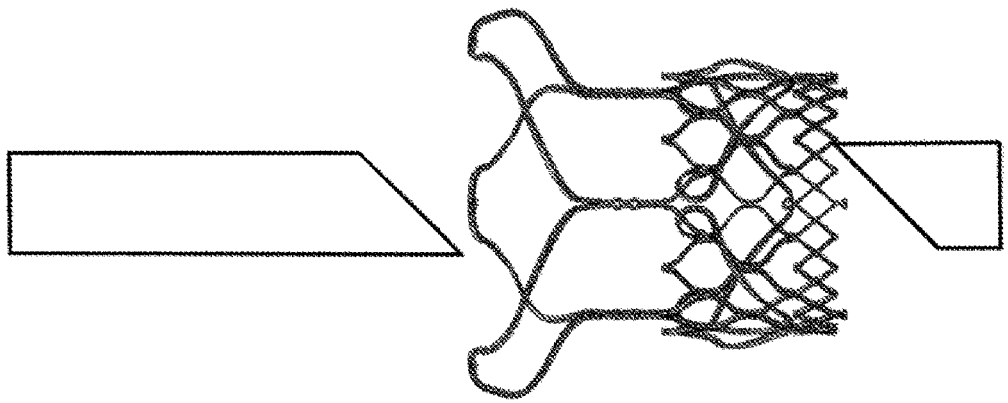
FIGS. 15A-15E show a schematic representation of the release of an exemplary embodiment of the heart valve prosthesis by means of an at least partially beveled catheter, in accordance with an embodiment. As illustrated herein, the arches of the compartmentalization clips are successively releasable upon the retracting of the catheter sleeve or introducer sheath.
Figure 15D:
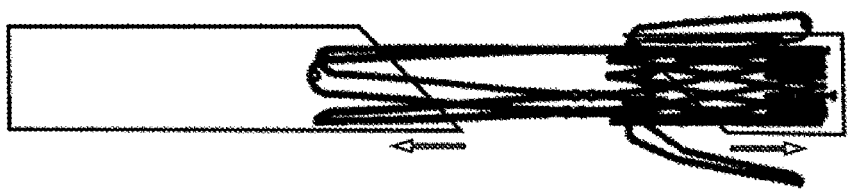
Figure 15C:
Figure 15B:
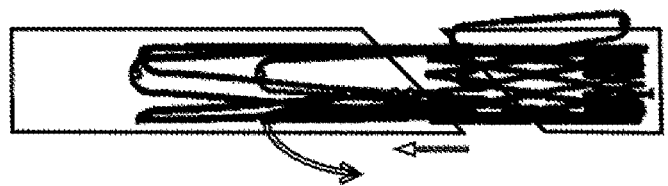
Figure 15A:

1 Frame structure of heart valve prosthesis;
2 Stent framework;
3 Compartmentalization clips;
4 Stabilization arches;
5 Separating layer;
6 Areas containing active substance/matrices.

DETAILED DESCRIPTION OF THE INVENTION

The invention solves the above-cited clinical problem by designing catheter-guided heart valve prostheses such that the infected areas are isolated from the bloodstream by compartmentalization clips. In embodiments, active substance-releasing matrices are affixed to the heart valve prosthesis which locally treat inflammation via compartmentalization (active agent-releasing heart valve prosthesis). The heart valve prosthesis is moreover configured such that the compartmentalization clips and structures attached thereto may engage around infectious deposits (vegetation) and thus prevent an embolization. Embodiments of these catheter-guided heart valve structures also may prevent an overall rare occurrence of postoperative PVE (1-1.5% in the first postoperative year).

The inventive solutions are further described in the paragraphs below.

According to a first aspect, the invention relates to an anchoring for heart valve prostheses, in particular for heart valve prostheses for the treatment, prevention and/or replacement of a heart valve, such as an inflamed, infected, thrombosed and/or degenerated heart valve. The anchoring exhibits a primary form and is able to be reversibly transformed into a delivery form for minimally invasive introduction of the anchoring into a patient's body. In embodiments, the transformation includes elastic deformation and/or compression of at least regions or elements of the anchoring. The anchoring may include a stent framework configured to attach to at least two heart valve leaflets at an inner side. The stent framework may include a proximal end and a distal end. The anchoring may further include at least two compartmentalization clips, each compartmentalization clip being connected with the stent framework at a first end region and having a free second end region. The compartmentalization clips may be arcuately shaped between the first and second end regions in the primary form of the anchoring.

According to a further embodiment, the compartmentalization clips may at least partially overlap the stent framework, particularly in a radial direction of the stent framework, in the primary form of the anchoring.

According to a further embodiment, the compartmentalization clips may be elastically foldable such that the compartmentalization clips may extend in at least substantially flat manner between the first and second end regions in the delivery form of the anchoring.

According to a further embodiment, the compartmentalization clips may include arms having an at least partial twisting in the primary form of the anchoring.

According to a further embodiment, the compartmentalization clips may include a first clip surface and a second clip surface oppositely disposed from the first clip surface, wherein the first clip surface at the free second end area of the compartmentalization clips is directed at least substantially radially inward, in particular toward a longitudinal axis of the anchoring, in both the primary form as well as the delivery form of the anchoring.

According to a further embodiment, the second surface at the second end area of the compartmentalization clips may be directed at least substantially radially outward in both the primary form as well as the delivery form of the anchoring.

According to a further embodiment, when in an implanted state, the anchoring is configured to hold (e.g., clamp) native leaflets and/or infectious and/or thrombotic deposits/vegetation of a diseased heart valve between the stent framework and the compartmentalization clips.

According to a further embodiment, the anchoring includes a separation structure connected with the stent framework and the compartmentalization clips such that the separation structure separates the areas of the native leaflets to be treated from the bloodstream when the anchoring is in the implanted state.

According to a further embodiment, the separation structure includes a first structural surface which is directed radially inward in the delivery form of the anchoring, in particular toward a longitudinal axis of the anchoring. The separation structure also includes a second structural surface opposite from the first structural surface. In embodiments, at least the second structural surface may include a matrix containing and may be configured for releasing antibiotic, antithrombotic and/or thrombolytic agents.

According to a further embodiment, the stent framework and the compartmentalization clips may be of a single-piece construction.

According to a further embodiment, the stent framework and/or the compartmentalization clips may be made from a compressible material.

According to a further embodiment, the stent framework and/or the compartmentalization clips may be made from a self-expanding material.

According to a further embodiment, the stent framework and the compartmentalization clips may be made from at least two connected or connectable pieces of a self-expandable material.

According to a further embodiment, the stent framework and the compart-mentalization clips may be made from at least two connected or connectable pieces. The stent framework may be made from a balloon-expandable material, and the compartmentalization clips may be made from a self-expandable material.

According to a further embodiment, the stent framework and/or the compartmentalization clips may include a shape memory alloy, such as nitinol.

According to a further embodiment, the at least two compartmentalization clips may overlap the stent framework in the primary form of the anchoring such that substantially no part of the compartmentalization clips protrudes beyond the distal end of the stent framework.

According to a further aspect, the invention relates to a catheter for introducing an anchoring for heart valve prostheses into the body of a patient. The catheter may aid in the anchoring being able to be introduced minimally invasively into the patient's body in a delivery form and transformed into an implanted state at the implantation site on the diseased heart valve. The anchoring may include a stent framework designed to attach to at least two heart valve leaflets on an inner side, wherein the stent framework has a proximal end and a distal end. The anchoring may further include at least two compartmentalization clips connected with the stent framework and which at least partially overlap the stent framework in the primary form of the anchoring in order to hold (i.e., clamp) native leaflets and/or infectious and/or thrombotic deposits/vegetation of the diseased heart valve between the stent framework and the compartmentalization clips. The catheter may include a catheter tip configured to be manipulated via a handle of the catheter such that the implant is incrementally releasable from the catheter tip.

According to a further embodiment, the catheter tip may be formed of a divided design such that the at least two compartmentalization clips may be incrementally released from the catheter tip one after the other and the stent framework then subsequently released.

According to a further embodiment, the partitioned catheter tip includes a tapered sleeve configured to cover the anchoring during introduction and may be retractable by means of the handle to incrementally release the compartmentalization clips.

According to a further embodiment, the catheter may be configured to rotate the anchoring by the handle in order to align the compartmentalization clips with the pockets/leaflets of the native valve.

According to a further aspect, the invention relates to a system for the treatment, prevention and/or replacement of a heart valve, in particular an inflamed, infected, thrombosed or degenerated heart valve. The system may include one of the above anchorings and one of the above catheters. The anchoring may be designed to be receivable in a catheter tip, particularly when the anchoring is in a delivery form. The catheter tip may be configured to accommodate the anchoring therein, particularly when the anchoring is in delivery form.

According to a further aspect, the invention relates to a method for the treatment, prevention and/or replacement of a heart valve, in particular an inflamed, infected, thrombosed or degenerated heart valve. The method may include the following steps:

introducing an anchoring at a location of the diseased heart valve via a catheter, the anchoring including a stent framework and two or more compartmentalization clips;

releasing the compartmentalization clips;

aligning the compartmentalization clips on a first side of the native leaflets of the diseased heart valve;

releasing the stent framework on a second side of the native leaflets opposite from the first side.

According to a further embodiment, the method further includes releasing antibiotic, antithrombotic, thrombolytic and/or cell growth-inhibiting agents, whereby the release ensues in situ at the location of the diseased heart valve.

According to a further embodiment, the compartmentalization clips are incrementally released one after the other from the catheter tip.

According to a further aspect, the invention relates to an anchoring for heart valve prostheses, in particular for heart valve prostheses for the treatment, prevention and/or replacement of a heart valve, in particular an inflamed, infected, thrombosed or degenerated heart valve. The anchoring exhibits a primary form, and the anchoring may be reversibly transformed, such as by elastic deformation and/or compression of at least regions or elements of the anchoring, into a delivery form for the minimally invasive introduction of the anchoring into the body of a patient. The anchoring may include a stent framework configured to attach at least two heart valve leaflets to an inner side, wherein the stent framework has a proximal end and a distal end. The anchoring may further include at least two stabilization arches that protrude beyond the distal end of the stent framework. The stabilization arches are configured to be supported on a vascular wall in the implanted state of the anchoring such that the anchoring may be centrally aligned in the blood vessel to be implanted subsequent the release of the stabilization arches.

According to a further embodiment, the length and/or shape of the at least two stabilization arches may be configured to be distinguishable in an X-ray and be able to be released one after the other during implantation.

According to a further embodiment, the stabilization arches include a proximal end connected to the distal end of the stent framework and a distal end protruding beyond the distal end of the stent framework. The stabilization arches may be connected together at the distal end by struts, diamond-like or other elements which are designed to increase the radial stability and enable a centralizing of the anchoring in the blood vessel to be implanted.

According to a further embodiment, the anchoring may include a separation structure connected to the stent framework such that the separation structure separates the areas of the native leaflets to be treated from the bloodstream in the expanded state of the anchoring.

According to a further embodiment, the separation structure includes an external matrix containing and configured to release antibiotic, antithrombotic and/or thrombolytic agents.

According to a further embodiment, the stent framework and the stabilization arches may be formed of a single-piece construction.

According to a further embodiment, the stent framework and/or the stabilization arches may be formed of a compressible material.

According to a further embodiment, the stent framework and/or the stabilization arches may be formed of a self-expanding material.

According to a further embodiment, the stent framework and/or the stabilization arches may be formed of a shape memory alloy, such as nitinol.

According to a further embodiment, the anchoring may include at least two compartmentalization clips, each connected with the stent framework at a first end region and having a free second end region. The compartmentalization clips may be arcuately shaped between the first and second end regions in the primary form of the anchoring.

According to a further embodiment, the compartmentalization clips at least partially overlap the stent framework in the primary form of the anchoring.

According to a further embodiment, the compartmentalization clips are foldable such that the compartmentalization clips extend in at least substantially flat manner between the first and second end regions in the delivery form of the anchoring.

According to a further aspect, the invention relates to an anchoring for heart valve prostheses, in particular for heart valve prostheses for the treatment, prevention and/or replacement of a heart valve, particularly an inflamed, infected, thrombosed or degenerated heart valve. The anchoring may exhibit a primary form and may be reversibly transformed, such as by elastic deformation and/or compression of at least regions or elements of the anchoring, into a delivery form for the minimally invasive introduction of the anchoring into the body of a patient. The anchoring may include a stent framework configured to attach to at least two heart valve leaflets at an inner side, wherein the stent framework has a proximal end and a distal end. The anchoring may further include at least two compartmentalization clips connected to the stent framework and which at least partially overlap the stent framework in the primary form of the anchoring in order to hold (i.e., clamp) native leaflets and/or infectious and/or thrombotic deposits/vegetation of the diseased heart valve between the stent framework and the compartmentalization clips. The anchoring may further include a separation structure connected with the stent framework and the compartmentalization clips such that when in the implanted state, the separation structure separates the areas of the native leaflets to be treated from the bloodstream.

According to a further embodiment, the separation structure includes a first structural surface which is directed radially inward in the delivery form, in particular toward a longitudinal axis of the anchoring, and a second structural surface opposite from the first structural surface. At least the second structural surface may include a matrix containing and may be configured to release antibiotic, antithrombotic and/or thrombolytic agents.

According to a further embodiment, the active substance-containing matrix is bioresorbable.

According to a further embodiment, the stent framework and the compartmentalization clips may be formed of a single-piece construction.

According to a further embodiment, the stent framework and/or the compartmentalization clips may be formed from a compressible material.

According to a further embodiment, the stent framework and/or the compartmentalization clips may be formed from a self-expandable material.

According to a further embodiment, the stent framework and the compartmentalization clips may be formed from at least two connected or connectible pieces of a self-expandable material.

According to a further embodiment, the stent framework and the compartmentalization clips may be formed from at least two connectable pieces connected together. The stent framework may be formed from a balloon-expandable material and the compartmentalization clips from a self-expandable material.

According to a further embodiment, the stent framework and/or the compartmentalization clips includes a shape memory alloy, such as nitinol.

According to a further embodiment, the at least two compartmentalization clips have a first end region which is connected to the stent framework and a free second end region. The compartmentalization clips may be arcuately shaped between the first and second end regions in the primary form of the anchoring.

According to a further embodiment, the compartmentalization clips are configured to at least partially overlap the stent framework in the primary form of the anchoring.

According to a further embodiment, the compartmentalization clips are configured to be foldable such that the compartmentalization clips may extend in at least substantially flat manner between the first and second end regions in the delivery form of the anchoring.

According to a further embodiment, the anchoring includes three compartmentalization clips.

According to a further embodiment, the at least two compartmentalization clips are radially spaced apart from each other and connected together via the stent framework in the expanded state of the anchoring.

According to a further embodiment, the stent framework includes a first cell structure including struts at its proximal end and a second cell structure including struts at its distal end, wherein the first and the second cell structure are of different designs.

According to a further embodiment, the first cell structure has a higher density of struts than the second cell structure.

According to a further embodiment, the anchoring may be formed from a shape memory alloy tube.

According to a further aspect, the invention relates to a heart valve prosthesis, in particular for heart valve prostheses for the treatment, prevention and/or replacement of a heart valve, particularly an inflamed, infected, thrombosed or degenerated heart valve. The heart valve prosthesis may include an anchoring as described above, including a stent framework with an inner side to which at least two heart valve leaflets may be affixed.

The technical implementations described herein include the following innovations and provide the following advantages over conventional catheter-guided heart valve prostheses.

For example, catheter-guided heart valve replacement is also possible using the embodiments described herein in the case of patients with bacterial endocarditis. This largely atraumatic procedure may be performed with lower risks in patients exhibiting high comorbidity. The active antibacterial substance concentrations in tissue able to be achieved through local application using the configurations as described above are significantly higher than those able to be achieved through systemic administration, as systemic administration of antibiotics is limited by toxic adverse drug reactions.

Embodiments of the inventive design to such a catheter-guided heart valve prosthesis can reduce the risk of postoperative endocarditis by prophylactic long-term antibiotic administration, thus protecting against infection of the heart valve prosthesis from microbial colonization, particularly bacteria, during the healing phase.

The herein described heart valve prosthesis also allows the treatment of a leaky heart valve (e.g., aortic valve insufficiency) as well as a narrowing of the heart valve (stenosis) by using compartmentalization clips to effect anchoring of the heart valve implant to the native heart valve leaflets.

The invention thus decisively expands the current indication spectrum of catheter-based heart valve surgery by enabling the treatment and prophylaxis of infective endocarditis (both native valve endocarditis (NVE) as well as prosthetic valve endocarditis (PVE)).

A significant innovation for heart valve prostheses intended for the treatment and/or prophylaxis of endocarditis compared to document WO 2020/074130 A1 is that the inventive heart valve prosthesis presented herein is composed of only one member (i.e., single piece construction). This feature is advantageous as the heart valve prostheses can be implanted in one step and thus with less expenditure of time and material, particularly because two separate members or elements do not need to be positively or non-positively aligned with each other. Furthermore, the problems described as arising at the connecting or contact points throughout the circumference of the heart valve prosthesis do not occur. A one-piece heart valve prostheses pursuant to the invention create a seamless connection between the two areas enfolding and compartmentalizing the infected and potentially infectious deposit-coated (vegetation) interior (luminal) and exterior (abluminal) of the native heart valve leaflets. Compartmentalization may be thereby improved. Further, by integrating an active matrix containing and configured to release antibiotic, antithrombotic and/or thrombolytic agents as described above, the one-piece heart valve prostheses presented herein enable higher local drug concentrations to be achieved.

Various embodiments of the inventive heart valve may include a single metal framework to be implanted. This single piece framework may also be assembled from multiple parts (e.g., during manufacture) in order to combine different materials, for example to combine specific material properties (self-expandable, balloon-expandable) and/or to realize certain stabilities or shapes. Various methods may be used to connect the individual parts into an integrated metal framework including welding, gluing, stitching, inserting, and others. In addition to the possibility of assembling this one metal framework from different parts, single-material and single-piece embodiments are also expressly noted (e.g., a workpiece laser-cut from a single shape memory alloy tube, which is brought into form in a subsequent shaping process).

In the catheter-guided implantation of heart valve prostheses, particularly when the heart valve prosthesis must be advanced a long way through the blood vessels to the site of implantation (e.g., in transfemoral introduction of the catheter into the blood system), it may be advantageous in light of the limited anatomical conditions for the heart valve prostheses to be able to be compressed (i.e., "crimped") to the smallest possible diameter for implantation. For instance, if the structures and materials of an existing two-piece heart valve prostheses (such as a stent framework and an abutment structure) for replacing infected heart valves are merely combined into one piece, the resulting one-piece solution consequently experiences a significant increase in circumference even when compressed/crimped.

In contrast, the inventive one-piece heart valve prostheses presented herein are constructed such that the heart valve prosthesis incorporates specially designed compartmentalization clips which, when inserted into the catheter prior to implantation, can be bent upward in a longitudinal (axial) direction and compressed together with the stent framework and such that the material does not overlap in axial height but is instead distributed over the axial length. This configuration enables the one-piece heart valve prosthetic to be introduced with catheters of common diameters. The upwardly bent compartmentalization clips may be released downward during implantation, in an incremental fashion. An incremental release may be advantageous since the folding over of the (potentially still compressed) arcuate compartmentalization clips may be accompanied by a temporary increase in the overall circumference of the heart valve prosthetic.

In addition to the folding of the compartmentalization arches, the arches may also be incrementally pushed downward in other inventive embodiments so that there is no significant increase in circumference during this downward alignment step.

For example, during implantation, as the still partially compressed heart valve prosthesis is pushed downward, the downwardly aligned compartmentalization arches, which may be connected with a continuous separating layer and possibly to a matrix containing active substance, will engage around and capture the infectious deposits (vegetation) adhering to/deposited on the native heart valve leaflets together with the infected heart valve leaflets themselves. The arches of the compartmentalization clips are thereby introduced into the pockets of the heart valves formed by the native heart valve leaflets with the vascular wall. The engaged area is further compressed upon the subsequent expansion and release of the stent framework and engaged areas thus compartmentalized. If integrated into the heart valve prosthesis, the at least one matrix containing active substance releases antibiotic agents into this compartmentalized area in order to locally treat the infection in this area.

In embodiments of the heart valve prosthesis, the compartmentalization clips may be affixed such that the arches do not rise and point upward from the "peaks" but rather in the "valleys" of diamond-like structures (e.g., when cut from one piece of material), with the shape set in the shaping process being nearly circular and pointing approximately tangentially outward in the expanded state and then forming a downward extending arch at the periphery of the stent framework. A 360° torsion is thereby imparted to the arches, which enables the material of the arches to absorb any deformations and associated related forces and tensions occurring during the process of the upward bending prior to implantation as well as the downward release during implantation without breaking or plastically deforming.

In other embodiments of the inventive heart valve prosthesis, the limbs of the compartmentalization clip arches extend far upwards after the shaping process and are then folded outwardly over a suitable radius of curvature or nearly tangentially downward 180°. In this way, the lowest portion of the compartmentalization clip may be folded back upward again for implantation so as to not position this area of the compartmentalization clips at the same axial height as the heart valve leaflets affixed within the stent framework during implantation (i.e., circumferential reduction during implantation).

In exemplary embodiments of the inventive heart flap prosthesis, (axially) upward aligned stabilization arches may furthermore be attached, these being releasable during implantation and (centrally) positioning the heart valve prosthesis in the vessel to be implanted in the at least partially expanded state so that the arches of the compartmentalization clips can be guided in all the native heart valve leaflets. In embodiments of the inventive heart valve prosthesis, these centralization arches may be connected in the axially upper region by arch-like or diamond-like elements or other types of elements in order to provide greater radial force to this area of the heart valve prosthesis. In addition, the inventive heart valve prostheses may be designed to cooperate with the delivery catheter system such that axial rotation of the heart valve prosthesis is possible during implantation in order to align the arches of the compartmentalization clips with the native heart valve leaflets.

Other variants of the embodiments described in the present disclosure may include, and are not limited to, the following.

1. A heart valve prostheses for the elimination and prevention of bacterial colonization of heart valve leaflets, in particular for therapeutic or prophylactic use in infectious endocarditis, characterized by the following features:
   - the heart valve prosthesis contains a radially compressible stent framework made from struts and arches;
   - at least two heart valve leaflets are luminally attached to the stent framework (inside);
   - the heart valve prosthesis contains at least two compartmentalization clips which in the expanded state are outwardly (abluminal) shaped from the distal (above) to the proximal (below), i.e., against the direction of blood flow, so as to engage around the native heart valve leaflets and any structures located thereon and position and anchor the stent framework in the axial direction;
   - the heart valve prosthesis has at least one separation structure connected to the stent framework and the compartmentalization clips and which separates/compartmentalizes the areas with the native leaflets to be treated from the bloodstream in the expanded state;
   - the heart valve prosthesis includes at least one matrix abluminal to the at least one separation structure able to contain and release antibiotic active substances;
   - the stent framework and/or the compartmentalization clips is/are designed together with the at least one separation structure such that the active substances are in particular released from the structures containing the active substances in the compartmentalized space; and
   - the heart valve prosthesis is implantable by means of a suitable device, e.g., via a catheter.

2. The heart valve prosthesis according to No. 1, wherein the stent framework and the compartmentalization clips are made from a single piece of compressible material.

3. The heart valve prosthesis according to No. 2, wherein the stent framework and the compartmentalization clips consist of a self-expandable material.

4. The heart valve prosthesis according to No. 1, wherein the stent framework and the compartmentalization clips are made from at least two connected pieces of at least one compressible material.

5. The heart valve prosthesis according to No. 4, wherein the stent framework and the compartmentalization clips are made from at least two connected pieces of a self-expandable material.

6. The heart valve prosthesis according to No. 5, wherein the stent framework and the compartmentalization clips are made from at least two connected pieces and the stent framework is made from a balloon-expandable material and the compartmentalization clips from a self-expandable material.

7. The heart valve prosthesis according to one of Nos. 1 to 6, wherein the stent framework and/or compartmentalization clips consist of a shape memory alloy.

8. The heart valve prosthesis according to one of Nos. 1 to 7, wherein the individual compart-mentalization clips are designed so as to be distinguishable in an X-ray.

9. The heart valve prosthesis according to one of Nos. 1 to 8, wherein the number of compartmentation clips is an integer multiple (n≥1) of the number of heart valve leaflets into which the valve is to be implanted.

10. The heart valve prosthesis according to one of Nos. 1 to 9, wherein the compartmentalization clips are shaped and oriented to point abluminal-proximal (outward-downward) in a partially expanded state so that the individual clips can be slipped into the space between the heart valve leaflets and the vessel wall.

11. The heart valve prosthesis according to one of Nos. 1 to 10, wherein the compartmentalization clips are arranged below the upper boundary of the uppermost row of diamond-like structures so that the downwardly arching compartmention clips do not or only slightly extend over the upper edge of the stent framework in the expanded state and thus do not obstruct the flow of blood and access to the inlets of the coronary vessels.

12. The heart valve prosthesis according to one of Nos. 1 to 11, wherein in compressed state, the compartmentation clips are in whole or in part folded over upward in the delivery catheter against the direction imparted in the shaping process such that the compartmentation clip arches are not situated at the same axial height as the stent framework but rather above the stent framework.

13. The heart valve prosthesis according to No. 12, wherein the compartmentalization clips, which are folded over upward in the compressed state, fold down automatically when released from the delivery catheter (in the direction of the shape imparted in the shaping process) in order to be aligned with the axial height of the stent framework.

14. The heart valve prosthesis according to one of Nos. 1 to 13, wherein the compartmentalization clips are designed such that in the expanded and downward folded-over state, the leaflets of the heart valve into which the heart valve prosthesis is to be implanted are clamped between the compartmentalization clips and the stent framework without affecting coronary flow.

15. The heart valve prosthesis according to one of Nos. 1 to 14, wherein the compartmentalization clips are designed such that in the expanded and folded-over state, the outer upper regions of two adjacent compart-mentalization clips respectively face each other so as to clamp and compartmentalize the largest possible areas of the leaflets, particularly in the area of the commissures of the heart valve to be replaced.

16. The heart valve prosthesis according to one of Nos. 1 to 15, wherein the compartmentalization clips are cut from a tube such that the arches are oriented upward away from the stent framework and bent downward in a plane from above (by a total of 180°).

17. The heart valve prosthesis according to one of Nos. 1 to 16, wherein the compartmentalization clips are cut from a tube such that the arches are oriented upward away from the stent framework and bent downward in a shaping process such that the arches make a full 360° rotation with respect to the stent framework. Note: The struts/limbs of the compartmentalization clips are thereby bent over the layer thickness (the layer thickness corresponding to the material thickness of the tube) (not strut width) and rotated a total of 360°.

18. The heart valve prosthesis according to one of Nos. 16 or 17, wherein the compartmentalization clips are designed in alternative embodiments to extend far distally (above, downstream) so as to centrally align and stabilize the heart valve prosthesis in the blood vessel to be implanted subsequent partial release.

19. The heart valve prosthesis according to one of Nos. 1 to 18, wherein at least two self-expandable arches are additionally formed on the stent framework which are released when the upper part of the heart valve prosthesis is released and directed outwardly and upwardly and which centrally align the entire heart valve prosthesis in the blood vessel through which the heart valve prosthesis is introduced.

20. The heart valve prosthesis according to No. 19, wherein the length and/or shape of the at least two stabilization arches is/are designed so as to be distinguishable in an X-ray and be able to be released one after the other during implantation.

21. The heart valve prosthesis according to No. 20, wherein the upper parts of the compartmentalization clips are connected by struts, diamond-like or other elements in order to increase the radial stability in the distal section and enable a centralizing of the heart valve prosthesis in the blood vessel to be implanted.

22. The heart valve prosthesis according to one of Nos. 1 to 19, wherein the at least one matrix containing active substance is bioresorbable.

23. The heart valve prosthesis according to one of Nos. 1 to 20, wherein the at least one matrix containing active substance is in the form of foils.

24. The heart valve prosthesis according to one of Nos. 1 to 21, wherein the compartmentalization clips together with the separating layers and the at least one active substance-releasing matrix capture infectious vegetation adhering to the native valve leaflets (together with the native valve leaflets themselves) in umbrella-like manner in the partially expanded state during implantation in order to compartmentalize them and prevent embolization of the vegetation.

25. The heart valve prosthesis according to one of Nos. 1 to 24, wherein the active substance-containing matrix/matrices on the compartmentalization clips are omitted in one embodiment and this embodiment serves in postoperative infection prophylaxis.

26. A delivery catheter for introducing the heart valve prosthesis according to one of Nos. 1 to 21 having a beveling or notching in the distal region of the introducer sheath, whereby the compartmentalization clips of the heart valve prosthesis can be incrementally released one after the other upon the retraction of the introducer sheath.

27. The delivery catheter according to No. 26, wherein the implant according to one of Nos. 1 to 25 is rotatable about its own longitudinal axis in the delivery catheter or with a part of the catheter in order to align the compartmentalization clips with the pockets of the native valve.

28. A heart valve prostheses for the elimination and prevention of bacterial colonization of heart valve leaflets, in particular for therapeutic or prophylactic use in infectious endocarditis, characterized by the following features:
  the heart valve prosthesis contains a stent framework made from struts and arches or self-contained forms,
  at least two heart valve leaflets are luminally attached to the stent framework (inside),
  the heart valve prosthesis contains at least two anchoring clips able to be outwardly (abluminal) folded from the distal (above) to the proximal (below); i.e., against the direction of blood flow, so as to engage (around) the native heart valve leaflets and any structures located thereon,
  the heart valve prosthesis has abluminal areas able to contain and release antibiotic agents,
  the heart valve prosthesis has at least one thin layer connected to the stent framework and to the clips and separating the areas containing active substance from the bloodstream,
  the heart valve prosthesis is implantable via a catheter.

29. The heart valve prosthesis according to No. 28, wherein the stent framework and the anchoring clips are made from a single piece of self-expandable material.

30. The heart valve prosthesis according to one of Nos. 28 or 29, wherein the stent framework is self-expandable.

31. The heart valve prosthesis according to one of Nos. 28 to 30, wherein the anchoring clips consist of a shape memory alloy.

32. The heart valve prosthesis according to one of Nos. 28 to 31, wherein the individual anchoring clips are distinguishable in an X-ray.

33. The heart valve prosthesis according to one of Nos. 28 to 32, wherein the number of anchoring clips is an integer multiple (n≥1) of the number of heart valve leaflets into which the valve is to be implanted.

34. The heart valve prosthesis according to one of Nos. 28 to 33, wherein the anchoring clips are shaped and oriented to point abluminal-proximal (outward-downward) in a partially expanded state so that the individual clips can be slipped into the space between the heart valve leaflets and the vessel wall.

35. The heart valve prosthesis according to one of Nos. 28 to 34, wherein the anchoring clips are arranged below the upper boundary of the uppermost row of diamond-like structures so that the downwardly arching anchoring clips do not or only slightly extend over the upper edge of the uppermost row of diamond-like structures in the expanded state and thus do not obstruct the flow of blood and access to the inlets of the coronary vessels.

36. The heart valve prosthesis according to one of Nos. 28 to 35, wherein the anchoring clips are designed such that in the expanded and folded-over state, the leaflets of the heart valve into which the heart valve prosthesis is to be implanted are clamped between the anchoring clips and the stent framework.

37. The heart valve prosthesis according to one of Nos. 28 to 36, wherein the anchoring clips are designed such that in the expanded and folded-over state, the outer upper regions of two adjacent anchoring clips respectively face each other so as to clamp and compartmentalize the largest possible areas of the leaflets, particularly in the area of the commissures of the heart valve to be replaced.

38. The heart valve prosthesis according to one of Nos. 28 to 37, wherein the at least one thin layer together with the anchoring clips enfold the leaflets of the heart valve into which the heart valve prosthesis is to be implanted in the expanded state and thus separate or compartmentalize them from the bloodstream.

39. The heart valve prosthesis according to one of Nos. 28 to 38, wherein the areas with antibiotic agents together with the thin layers and the anchoring clips enfold the leaflets of the heart valve into which the heart valve prosthesis is to be implanted in the expanded state and thus separate or compartmentalize them from the bloodstream.

40. The heart valve prosthesis according to one of Nos. 28 to 39, wherein at least two expandable stabilization arches are formed on the stent framework which centrally align the heart valve prosthesis in the blood vessel through which the heart valve prosthesis is led when introduced via a catheter.

41. The heart valve prosthesis according to one of Nos. 28 to 40, wherein the in the broadest sense cylindrical stent framework of the heart valve prosthesis exhibits such a low height that that it remains below the outlet of the coronary arteries and thereby facilitates any subsequent access to the coronary arteries that may be necessary via cardiac catheter.

42. The heart valve prosthesis according to one of Nos. 28 to 41, wherein the areas containing active substance are in the form of foils.

43. The heart valve prosthesis according to one of Nos. 28 to 42, wherein the areas containing active substance are bioresorbable.

44. The heart valve prosthesis according to one of Nos. 28 to 43, wherein the anchoring clips together with the thin layers and active substance-releasing areas capture infectious vegetation adhering to the valves in umbrella-like manner in the partially expanded state during implantation and prevent embolization.

45. The heart valve prosthesis according to one of Nos. 28 to 44, wherein a compartment largely shielded from the blood flow is formed during implantation by the anchoring clips downwardly aligned to the outside of the stent framework in that the antibiotic agents for the treatment of endocarditis can be released and remain in high concentration.

46. The heart valve prosthesis according to one of Nos. 28 to 45, wherein the at least two stabilization arches (No. 19) can also be omitted in an embodiment.

47. The heart valve prosthesis according to one of Nos. 28 to 46, wherein the active substance-containing areas on the anchoring clips are omitted in a third embodiment and this embodiment serves in postoperative infection prophylaxis.

48. A delivery catheter for introducing the heart valve prosthesis having a beveling or notching in the distal region of the introducer sheath, whereby the anchoring clips of the non-expanded heart valve prosthesis can be incrementally released one after the other.

49. The delivery catheter according to No. 48, wherein the implant pursuant to one of Nos. 1 to 25 is rotatable about its own longitudinal axis in or with a part of the catheter in order to align the anchoring clips with the pockets of the native valve.

50. An anchoring for heart valve prostheses for the treatment and/or replacement of an inflamed and/or infected heart valve, wherein the anchoring can be introduced minimally invasively into the patient's body in a compressed state and can be transformed into an expanded state at the implantation site on the diseased heart valve and includes the following:
  a stent framework (2) designed to attach at least two heart valve leaflets to an inner side, wherein the stent framework has a proximal end and a distal end;
  at least two compartmentalization clips (3) connected to the stent framework and designed to protrude beyond the distal end of the stent framework (2) in the compressed state of the anchoring as well as at least partially overlap the stent framework (2) in the expanded state of the heart valve prosthesis,
  wherein the compartmentalization clips (3) each have at least one arm designed to invert and twist during transition between the compressed state and the expanded state.

51. The anchoring according to No. 50, wherein the compartmentalization clips (3) have a proximal end connected to the distal end of the stent framework (2) and a distal end which protrudes beyond the distal end of the stent framework in the compressed state, wherein the compartmentalization clips (2) have a first surface and a second surface oppositely disposed from the first surface, and wherein the first surface at the distal end of the compartmentalization clips is directed substantially radially inward in the compressed state and in the expanded state.

52. The anchoring according to No. 51, wherein the second surface at the distal end of the compartmentalization clips is directed substantially radially outward in the compressed state and in the expanded state.

53. The anchoring according to one of Nos. 50 to 52, wherein the anchoring is designed to hold, in particular clamp native leaflets of the diseased heart valve between the stent framework and the compartmentalization clips (3) in the expanded state.

54. The anchoring according to one of Nos. 50 to 53 having a separation structure connected to the stent framework (2) and the compartmentalization clips (3) such that the separation structure separates the areas of the native leaflets to be treated from the bloodstream in the expanded state.

55. The anchoring according to No. 54, wherein the separation structure includes an at least external matrix which contains and can release antibiotic agents.

56. The anchoring according to one of Nos. 50 to 55, wherein the stent frame-work and the compartmentalization clips are of a single-piece construction.

57. The anchoring according to one of Nos. 50 to 56, wherein the stent frame-work and/or the compartmentalization clips is/are made from a compressible material.

58. The anchoring according to one of Nos. 50 to 57, wherein the stent frame-work and/or the compartmentalization clips is/are made from a self-expanding material.

59. The anchoring according to one of Nos. 50 to 55, wherein the stent frame-work and the compartmentalization clips are made from at least two connected or connectible pieces of a self-expandable material.

60. The anchoring according to one of Nos. 50 to 55, wherein the stent frame-work and the compartmentalization clips are made from at least two connectable pieces connected together and the stent framework is made from a balloon-expandable material and the compartmentalization clips from a self-expandable material.

61. The anchoring according to one of Nos. 50 to 60, wherein the stent frame-work and/or the compartmentalization clips consist of a shape memory alloy, in particular nitinol.

62. The anchoring according to one of Nos. 50 to 61, wherein the at least two compartmentalization clips (3) overlap the stent framework (2) in the expanded state of the anchoring such that no part of the compartmentalization clips protrudes beyond the distal end of the stent framework (2).

63. A catheter for introducing an anchoring for heart valve prostheses into the body of a patient, wherein the catheter aids in the anchoring being able to be introduced minimally invasively into the patient's body in a compressed state and transformed into an expanded state in the implantation site on the diseased heart valve, and the anchoring includes the following:
    a stent framework (2) designed to attach at least two heart valve leaflets to an inner side, wherein the stent framework has a proximal end and a distal end;
    at least two compartmentalization clips (3) connected to the stent framework and which protrude over the distal end of the stent framework (2) in the compressed state of the anchoring as well as at least partially overlap the stent framework (2) in the expanded state of the anchoring,
    wherein the catheter has a catheter tip able to be manipulated via a handle of the catheter (20) such that the implant (1) is incrementally releasable from the catheter tip.

64. The catheter according to No. 63, wherein the catheter tip is designed such that the at least two compartmentalization clips (3) can be incrementally released from the catheter tip one after the other.

65. The catheter according to No. 64, wherein the catheter tip has a tapered sleeve which is designed to completely cover the anchoring during introduction and which is retractable by means of the handle in order to incrementally release the compartmentalization clips.

66. The catheter according to one of Nos. 63 to 66, wherein the catheter is designed to rotate the anchoring by the handle in order to align the compartmentalization clips with the pockets/leaflets of the native valve.

67. A system for the treatment or replacement of an inflamed, thrombosed or degenerated heart valve which has an anchoring according to one of Nos. 50 to 62 and a catheter according to one of Nos. 63 to 66, wherein the anchoring is designed to be receivable in the catheter tip, particularly in its compressed state, and wherein the catheter tip is designed to accommodate the anchoring (1), particularly in its compressed state.

68. A method for the treatment or replacement of an inflamed, thrombosed or degenerated heart valve, wherein the method includes the following:
    introducing an anchoring according to one of Nos. 50 to 62 via a catheter according to one of Nos. 63 to 66;
    releasing the compartmentalization clips (3);
    aligning the compartmentalization clips on a first side of the native leaflets of the diseased heart valve;
    releasing the stent framework (2) on a second side of the native leaflets opposite from the first side.

69. The method according to No. 68, wherein the method further includes the method step of releasing antimicrobial, antithrombotic and cell growth-inhibiting agents, whereby the release ensues in situ.

70. The method according to No. 68 or 69, wherein the compartmentalization clips (3) are incrementally released one after the other.

71. An anchoring for heart valve prostheses for the treatment and/or replacement of an inflamed and/or infected heart valve, wherein the anchoring can be introduced minimally invasively into the patient's body in a compressed state and can be transformed into an expanded state at the implantation site on the diseased heart valve and includes the following:
    a stent framework (2) designed to attach at least two heart valve leaflets to an inner side, wherein the stent framework has a proximal end and a distal end;
    at least two stabilization arches (4) which protrude beyond the distal end of the stent framework (2) and are designed to be supported on a vascular wall in the expanded state of the anchoring such that the anchoring is centrally aligned in the blood vessel to be implanted subsequent the release of the stabilization arches (4).

72. The anchoring according to No. 71, wherein the length and/or shape of the at least two stabilization arches is/are designed so as to be distinguishable in an X-ray and be able to be released one after the other during implantation.

73. The anchoring according to No. 71 or 72, wherein the stabilization arches have a proximal end connected to the distal end of the stent framework (2) and a distal end which protrudes beyond the distal end of the stent framework, and wherein the stabilization arches are connected together at the distal end by struts, diamond-like or other elements which are designed to increase the radial stability and enable a centralizing of the anchoring in the blood vessel to be implanted.

74. The anchoring according to one of Nos. 71 to 73 having a separation structure connected to the stent framework (2) such that the separation structure separates the areas of the native leaflets to be treated from the bloodstream in the expanded state.

75. The anchoring according to No. 74, wherein the separation structure includes an at least external matrix which contains and can release antibiotic agents.

76. The anchoring according to one of Nos. 71 to 75, wherein the stent framework and the stabilization arches are of a single-piece construction.

77. The anchoring according to one of Nos. 71 to 76, wherein the stent framework and/or the stabilization arches is/are made from a compressible material.

78. The anchoring according to one of Nos. 71 to 77, wherein the stent framework and/or the stabilization arches is/are made from a self-expanding material.

79. The anchoring according to one of Nos. 71 to 78, wherein the stent framework and/or the stabilization arches consist of a shape memory alloy, in particular nitinol.

80. An anchoring for heart valve prostheses for the treatment and/or replacement of an inflamed and/or infected heart valve, wherein the anchoring can be introduced minimally invasively into the patient's body in a compressed state and can be transformed into an expanded state at the implantation site on the diseased heart valve and includes the following:
    a stent framework (2) designed to attach at least two heart valve leaflets to an inner side, wherein the stent framework has a proximal end and a distal end;

at least two compartmentalization clips (3) connected to the stent framework and designed to protrude beyond the distal end of the stent framework (2) in the compressed state of the anchoring as well as at least partially overlap the stent framework (2) in the expanded state of the anchoring, a separation structure connected to the stent framework (2) and the compartmentalization clips (3) such that the separation structure separates the areas of the native leaflets to be treated from the bloodstream in the expanded state.

81. The anchoring according to No. 80, wherein the separation structure includes an at least external matrix which contains and can release antibiotic agents.

82. The anchoring according to No. 81, wherein the at least matrix containing active substance is bioresorbable.

83. The anchoring according to one of Nos. 80 to 82, wherein the anchoring is designed to hold, in particular clamp, native leaflets of the diseased heart valve between the stent framework and the compartmentalization clips (3) in the expanded state.

84. The anchoring according to one of Nos. 80 to 83, wherein the stent framework and the compartmentalization clips are of a single-piece construction.

85. The anchoring according to one of Nos. 80 to 84, wherein the stent framework and/or the stabilization arches is/are made from a compressible material.

86. The anchoring according to one of Nos. 80 to 85, wherein the stent framework and/or the stabilization arches is/are made from a self-expanding material.

87. The anchoring according to one of Nos. 80 to 86, wherein the stent frame-work and the compartmentalization clips are made from at least two connected or connectible pieces of a self-expandable material.

88. The anchoring according to one of Nos. 80 to 87, wherein the stent frame-work and the compartmentalization clips are made from at least two connectable pieces connected together and the stent framework is made from a balloon-expandable material and the compartmentalization clips from a self-expandable material.

89. The anchoring according to one of Nos. 80 to 88, wherein the stent frame-work and/or the compartmentalization clips consist of a shape memory alloy, in particular nitinol.

90. The anchoring according to one of Nos. 80 to 89, wherein the compartmentalization clips (3) each have at least one arm designed to invert and twist during transition between the compressed state and the expanded state.

91. The anchoring according to No. 90, wherein the at least two compartmentalization clips (3) overlap the stent framework (2) in the expanded state of the anchoring such that no part of the compartmentalization clips protrudes beyond the distal end of the stent framework (2).

92. The anchoring according to one of Nos. 50 to 62 or 71 to 91, wherein the anchoring includes three compartmentalization clips (3).

93. The anchoring according to one of Nos. 50 to 62 or 71 to 92, wherein the at least two compartmentalization clips (3) are radially spaced apart from each other and connected together via the stent framework (2) in the expanded state.

94. The anchoring according to one of Nos. 50 to 62 or 71 to 93, wherein the stent framework exhibits a first cell structure made of struts at its proximal end and a second cell structure made of struts at its distal end, wherein the first and the second cell structure are of different designs.

95. The anchoring according to No. 94, wherein the first cell structure has a higher density of struts than the second cell structure.

96. The anchoring according to one of Nos. 50 to 62 or 71 to 95, wherein the anchoring is cut from a shape memory alloy tube.

The invention claimed is:

1. An anchoring for a heart valve prosthesis for one of treatment, prevention, and replacement of a heart valve, in particular one of an inflamed, infected, thrombosed, and degenerated heart valve, the anchoring comprising:
   a stent framework configured for attaching at least two heart valve leaflets to an inner side, wherein the stent framework has a proximal end and a distal end; and
   at least two compartmentalization clips, each one of the at least two compartmentalization clips being connected with the stent framework at a first end region and having a free second end region, wherein the anchoring exhibits a primary form and is able to be reversibly transformed into a delivery form for minimally invasive introduction of the anchoring into a body of a patient by at least one of elastic deformation and compression of at least one of regions and elements of the anchoring,
   wherein the compartmentalization clips are arcuately shaped between the first and second end regions in the primary form of the anchoring,
   wherein the compartmentalization clips are configured to be elastically folded over such that the compartmentalization clips extend in a substantially flat manner between the first and second end regions in the delivery form of the anchoring,
   wherein the anchoring further comprises a separation structure connected with the stent framework and the compartmentalization clips such that the separation structure separates areas of native heart valve leaflets to be treated from a bloodstream when the anchoring is in an implanted state,
   wherein the compartmentalization clips comprise arms having an at least partial twisting in the primary form of the anchoring,
   wherein the compartmentalization clips include a first clip surface and a second clip surface oppositely disposed from the first clip surface, and
   wherein the first clip surface at the free second end area of the compartmentalization clips is directed substantially radially inward toward a longitudinal axis of the anchoring, in both the primary and delivery forms of the anchoring.

2. The anchoring of claim 1,
   wherein the compartmentalization clips at least partially overlap the stent framework in the radial and proximal direction of the stent framework in the primary form of the anchoring.

3. The anchoring of claim 1,
   wherein the compartmentalization clips comprise arms having an at least partial twisting in the primary form of the anchoring, and
   wherein the compartmentalization clips include a first clip surface and a second clip surface oppositely disposed from the first clip surface, and
   wherein the first clip surface is directed outward and the second clip surface directed inward in the primary form of the anchoring and the first surface is directed inward and the second surface directed outward in the delivery form of the anchoring.

4. The anchoring one of claim 1, wherein the anchoring is designed to hold and clamp at least one of native heart valve leaflets and, infectious deposits, infectious vegetation, thrombotic deposits, and thrombotic vegetation of the diseased heart valve between the stent framework and the compartmentalization clips when the anchoring is in an implanted state, and
 wherein the separation structure includes a first structural surface directed radially inward toward a longitudinal axis of the anchoring in the delivery form of the anchoring, and a second structural surface opposite from the first structural surface, and
 wherein the second structural surface comprises a matrix releasably containing at least one of antibiotic, antithrombotic, and thrombolytic agents.

5. The anchoring of claim 1, wherein the stent framework and the at least two compartmentalization clips are formed from at least one of:
 a single-piece construction,
 a compressible material,
 a self-expanding material,
 at least two connectable pieces of a self-expandable material,
 at least two connectable pieces,
 a balloon-expandable material, and
 a shape memory alloy including nitinol.

6. The anchoring of claim 1, wherein the at least two compartmentalization clips overlap the stent framework in the primary form of the anchoring such that no part of the compartmentalization clips protrudes beyond the distal end of the stent framework.

7. The anchoring of claim 1,
 wherein the at least two compartmentalization clips are radially spaced apart from each other and connected together via the stent framework in an expanded state of the anchoring,
 wherein the stent framework exhibits a first cell structure formed of struts at its proximal end and a second cell structure formed of struts at its distal end,
 wherein the first and the second cell structure are of different designs,
 wherein the first cell structure has a higher density of struts than the second cell structure, and
 wherein the anchoring is cut from a shape memory alloy tube.

8. An anchoring for a heart valve prosthesis for one of treatment, prevention, and replacement of a heart valve, in particular an inflamed, infected, thrombosed, and degenerated heart valve, the anchoring comprising:
 a stent framework configured for attaching at least two heart valve leaflets to an inner side, wherein the stent framework has a proximal end and a distal end; and
 at least two compartmentalization clips, each one of the at least two compartmentalization clips being connected with the stent framework,
 wherein each one of the at least two compartmentalization clips being configured to at least partially overlap the stent framework in a primary form of the anchoring to hold and clamp at least one of native heart valve leaflets and infectious deposits, infectious vegetation, thrombotic deposits, and thrombotic vegetation of the native heart valve between the stent framework and at least one of the at least two compartmentalization clips,
 wherein the anchoring exhibits a primary form,
 wherein the anchoring is configured to be reversibly transformable, by at least one of elastic deformation and compression of at least one of regions and elements of the anchoring, into a delivery form for minimally invasive introduction of the anchoring into a body of a patient,
 wherein each one of the at least two compartmentalization clips includes a first end region, which first end region is connected with the stent framework, and a free second end region,
 wherein each one of the at least two compartmentalization clips is able to be folded over such that the at least two compartmentalization clips extend in a substantially flat manner between the first and second end regions in the delivery form of the anchoring,
 wherein the anchoring further comprises a separation structure connected with the stent framework and the at least two compartmentalization clips such that, when in an implanted state, the separation structure separates areas of native heart valve leaflets to be treated from a bloodstream,
 wherein the separation structure includes a first structural surface directed radially inward toward a longitudinal axis of the anchoring in the delivery form, and a second structural surface opposite from the first structural surface,
 wherein at least the second structural surface comprises a matrix releasably containing at least one of an antibiotic, antithrombotic, and thrombolytic agents, and
 wherein the at least one active substance-containing matrix is bioresorbable.

9. The anchoring of claim 8,
 wherein the stent framework and the at least two compartmentalization clips are formed from at least one of:
 a single-piece construction,
 a compressible material,
 a self-expandable material,
 at least two connectable pieces of a self-expandable material,
 at least two connectable pieces,
 a balloon-expandable material, and
 a shape memory alloy including nitinol, and
 wherein the at least two compartmentalization clips partially overlap the stent framework in the primary form of the anchoring.

10. The anchoring of claim 8,
 wherein the at least two compartmentalization clips are radially spaced apart from each other and connected together via the stent framework in an expanded state of the anchoring,
 wherein the stent framework exhibits a first cell structure formed of struts at its proximal end and a second cell structure formed of struts at its distal end,
 wherein the first and the second cell structure are of different designs,
 wherein the first cell structure has a higher density of struts than the second cell structure, and
 wherein the anchoring is cut from a shape memory alloy tube.

11. An anchoring for a heart valve prosthesis for one of treatment, prevention, and replacement of a heart valve, in particular one of an inflamed, infected, thrombosed, and degenerated heart valve, the anchoring comprising:
 a stent framework configured for attaching at least two heart valve leaflets to an inner side, wherein the stent framework has a proximal end and a distal end; and
 at least two compartmentalization clips, each one of the at least two compartmentalization clips being connected with the stent framework at a first end region and having a free second end region, wherein the anchoring exhibits a primary form and is able to be reversibly transformed into a delivery form for minimally invasive introduction of the anchoring into a body of a patient by at least one of elastic deformation and compression of at least one of regions and elements of the anchoring, wherein the compartmentalization clips are arcuately shaped between the first and second end regions in the primary form of the anchoring, wherein the compartmentalization clips are configured to be elastically folded over such that the compartmentalization clips extend in a substantially flat manner between the first and second end regions in the delivery form of the anchoring, wherein the anchoring further comprises a separation structure connected with the stent framework and the compartmentalization clips such that the separation structure separates areas of native heart valve leaflets to be treated from a bloodstream when the anchoring is in an implanted state, wherein the compartmentalization clips comprise arms having an at least partial twisting in the primary form of the anchoring, and wherein the compartmentalization clips include a first clip surface and a second clip surface oppositely disposed from the first clip surface, and wherein the first clip surface is directed outward and the second clip surface directed inward in the primary form of the anchoring and the first surface is directed inward and the second surface directed outward in the delivery form of the anchoring.

12. The anchoring of claim 11,
wherein the compartmentalization clips at least partially overlap the stent framework in the radial and proximal direction of the stent framework in the primary form of the anchoring.

13. The anchoring one of claim 11, wherein the anchoring is designed to hold and clamp at least one of native heart valve leaflets and, infectious deposits, infectious vegetation, thrombotic deposits, and thrombotic vegetation of the diseased heart valve between the stent framework and the compartmentalization clips when the anchoring is in an implanted state, and wherein the separation structure includes a first structural surface directed radially inward toward a longitudinal axis of the anchoring in the delivery form of the anchoring, and a second structural surface opposite from the first structural surface, and wherein the second structural surface comprises a matrix releasably containing at least one of antibiotic, antithrombotic, and thrombolytic agents.

14. The anchoring of claim 11, wherein the stent framework and the at least two compartmentalization clips are formed from at least one of:
a single-piece construction,
a compressible material,
a self-expanding material,
at least two connectable pieces of a self-expandable material,
at least two connectable pieces,
a balloon-expandable material, and
a shape memory alloy including nitinol.

15. The anchoring of claim 11, wherein the at least two compartmentalization clips overlap the stent framework in the primary form of the anchoring such that no part of the compartmentalization clips protrudes beyond the distal end of the stent framework.

16. The anchoring of claim 11,
wherein the at least two compartmentalization clips are radially spaced apart from each other and connected together via the stent framework in an expanded state of the anchoring, wherein the stent framework exhibits a first cell structure formed of struts at its proximal end and a second cell structure formed of struts at its distal end, wherein the first and the second cell structure are of different designs, wherein the first cell structure has a higher density of struts than the second cell structure, and wherein the anchoring is cut from a shape memory alloy tube.

17. An anchoring for a heart valve prosthesis for one of treatment, prevention, and replacement of a heart valve, in particular one of an inflamed, infected, thrombosed, and degenerated heart valve, the anchoring comprising:

a stent framework configured for attaching at least two heart valve leaflets to an inner side, wherein the stent framework has a proximal end and a distal end; and at least two compartmentalization clips, each one of the at least two compartmentalization clips being connected with the stent framework at a first end region and having a free second end region, wherein the anchoring exhibits a primary form and is able to be reversibly transformed into a delivery form for minimally invasive introduction of the anchoring into a body of a patient by at least one of elastic deformation and compression of at least one of regions and elements of the anchoring, wherein the compartmentalization clips are arcuately shaped between the first and second end regions in the primary form of the anchoring, wherein the compartmentalization clips are configured to be elastically folded over such that the compartmentalization clips extend in a substantially flat manner between the first and second end regions in the delivery form of the anchoring, wherein the anchoring further comprises a separation structure connected with the stent framework and the compartmentalization clips such that the separation structure separates areas of native heart valve leaflets to be treated from a bloodstream when the anchoring is in an implanted state, wherein the anchoring is designed to hold and clamp at least one of native heart valve leaflets and, infectious deposits, infectious vegetation, thrombotic deposits, and thrombotic vegetation of the diseased heart valve between the stent framework and the compartmentalization clips when the anchoring is in an implanted state, and wherein the separation structure includes a first structural surface directed radially inward toward a longitudinal axis of the anchoring in the delivery form of the anchoring, and a second structural surface opposite from the first structural surface, and wherein the second structural surface comprises a matrix releasably containing at least one of antibiotic, antithrombotic, and thrombolytic agents.

18. The anchoring of claim 17, wherein the stent framework and the at least two compartmentalization clips are formed from at least one of:
a single-piece construction,
a compressible material,
a self-expanding material, at least two connectable pieces of a self-expandable material,
at least two connectable pieces,
a balloon-expandable material, and
a shape memory alloy including nitinol.

19. The anchoring of claim 17, wherein the at least two compartmentalization clips overlap the stent framework in the primary form of the anchoring such that no part of the compartmentalization clips protrudes beyond the distal end of the stent framework.

20. The anchoring of claim 17,
wherein the at least two compartmentalization clips are radially spaced apart from each other and connected together via the stent framework in an expanded state of the anchoring,
wherein the stent framework exhibits a first cell structure formed of struts at its proximal end and a second cell structure formed of struts at its distal end,
wherein the first and the second cell structure are of different designs,
wherein the first cell structure has a higher density of struts than the second cell structure, and
wherein the anchoring is cut from a shape memory alloy tube.

* * * * *